United States Patent [19]

Townsend et al.

[11] Patent Number: 5,840,743
[45] Date of Patent: Nov. 24, 1998

[54] MODIFIED BENZIMIDAZOLE NUCLEOSIDES AS ANTIVIRAL AGENTS

[75] Inventors: Leroy B. Townsend; John C. Drach, both of Ann Arbor, Mich.; George A. Freeman, Raleigh, N.C.

[73] Assignees: The Regents of the University of Michigan, Ann Arbor, Mich.; Glaxo Wellcome Inc., Research Triangle Park, N.C.

[21] Appl. No.: 786,696

[22] Filed: Jan. 22, 1997

Related U.S. Application Data

[60] Provisional application No. 60/010,463 Jan. 23, 1996.
[51] Int. Cl.[6] .................. A61K 31/415; C07D 405/04
[52] U.S. Cl. .................. 514/395; 514/394; 548/304.7
[58] Field of Search .................. 548/304.7; 514/394, 514/395

[56] References Cited

U.S. PATENT DOCUMENTS 5,248,672  9/1993  Townsend et al. .
5,360,795  11/1994  Townsend et al. .

FOREIGN PATENT DOCUMENTS 0576227  12/1993  European Pat. Off. .
WO 91/01325  2/1991  WIPO .
WO 96/01833  1/1996  WIPO .

OTHER PUBLICATIONS

Atrazhev et al., "2'–Deoxyribonucleoside 5'–triphosphates Chemically Modified in the base and sugar moieties as Substrates for DNA biosynthesis in vitro" *Chemical Abstracts.*(1988) 108 (13):284 (abstract No. 108680j).
Blank, H. U. et al., "Uber die Tritylierung von Adenosin- -Derivate." *Liebigs Ann. Chem.* (1970), 742, 34–42.
Chu, C. K. et al., "Nucleosides 135. Synthesis of Some 9–(2–deoxy–2–fluoro–β–D–arabinofurnosyl)–9H–purines and Their Biological Activities."*Chem. Pharm. Bull.* (1989), 37, 336.
Codington, J.F. et al., "Synthesis of 2'–Flurothymidine, 2'–fluorodeoxyuridine, and Other 2'–Halogeno–2'–Deoxy Nucleosides"*Org. Chem.* (1964) , vol. 29, pp. 558.
Cook et al. J. Biol. "Crystallization and Preliminary X–ray Investigation of Recombinant *Lactobacillus leichmannii* Nucleoside Deoxyribosyltransferase" *Chem.*(1990) , vol. 265, p. 2682.
Devivar et al., "Benzimidazole Ribonucleotides: Design, Synthesis, and Antiviral Activity of Certain 2–(Alkylthio)– and 2–(Benzylthio)–5,6–dichloro–(β–D–ribofuranosyl) benzimidazoles" *J. Med. Chem.* (1994)37(18):2942–2949.
Drach, J. C. et al., Fifth International Conference on Antiviral Research Vancouver, British Columbia; Abstract No. 12, Mar. 8–13, 1992.
Drach, J. C. et al., Fifth International Conference on Antiviral Research Vancouver, British Columbia; Abstract No. 105, Mar..8–13, 1992.
Dyatkins et al, "Nucleosides of Fluoro sugars. etc"CA 105:24554 (1986).
Drach, J. C. et al., Fifth International Conference on Antiviral Research Vancouver, British Columbia; Abstract No. 106, Mar. 8–13, 1992.
Drach J. C. et al., Fifth International Conference on Antiviral Research Vancouver, British Columbia; Abstract No. 107, Mar. 8–13, 1992.
Drach, J. C. et al., Fifth International Conference on Antiviral Research Vancouver, British Columbia; Abstract No. 108, Mar. 8–13, 1992.
Drach, J. C. et al., Fifth International Conference on Antiviral Research Vancouver, British Columbia; Abstract No. 109, Mar. 8–13, 1992.
Drach, J. C. et al., Fifth International Conference on Antiviral Research Vancouver, British Columbia; Abstract No. 110, Mar. 8–13, 1992.
Dyatkina et al., "Nucleosides of fluoro sugars. XV. Synthesis of 2', 3'–dideoxy–3'–fluroro–D–ribofuranosyl benzimidazole –a New Fluorosugar Purine Nucleoside Analog." *Chem. Abst.*(1986)105 (3):670 (abstract no. 24554w).
Gadler, H. "Nucleic Acid Hybridization for Measurement of Effects of Antiviral Compounds on Human Cytomegalovirus DNA Replication" *Antimicrobial Agents and Chemotherapy* (1983), vol. 24 pp. 370–374.

(List continued on next page.)

*Primary Examiner*—Patricia L. Morris
*Attorney, Agent, or Firm*—Morrison & Foerster LLP

[57] ABSTRACT

This invention pertains to nucleoside analogs which have antiviral activity and improved metabolic stability. More specifically, this invention pertains to modified sugar benzimidazole nucleosides, as exemplified by compounds such as benzimidazole nucleosides possessing a fluorinated sugar-like moiety (for example, a 2'-fluoro-furanosyl moiety or a 3'-fluoro-furanosyl moiety), and may be represented by the following formula,

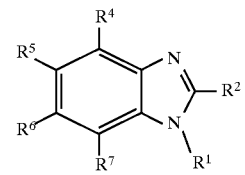

wherein $R^1$ is a fluorinated sugar-like moiety; and $R^2$, $R^4$, $R^5$, $R^6$ and $R^7$ are benzimidazole substituents, such as —H, halogens (e.g., —F, —Cl, —Br, —I), —$NO_2$, —$NR_2$ (where R is independently —H or an alkyl group having 1–6 carbon atoms), —OR (where R is —H or an alkyl group having 1–6 carbon atoms), —SR (where R is —H or a hydrocarbyl of 1–10 carbon atoms), and —$CF_3$. In one embodiment, $R^1$ is 2'-fluoro-furanosyl or 3'-fluoro-furanosyl; $R^2$ is —H, —F, —Cl, —Br, —I, or —$NR_2$, wherein R is independently —H or an alkyl group having 1–6 carbon atoms; $R^4$, $R^5$, $R^6$ and $R^7$ are independently —H, —F, —Cl, —Br, or —I.

13 Claims, 3 Drawing Sheets

OTHER PUBLICATIONS

Good et al., *Antiviral Research (Suppl. 1)*.(1994), vol. 23, p. 103.

Gudmundsson et al., "Palladium Catalysed Coupling of 2,6–Dichloro–3–iodoimidazo [1,2–a]pyridine and 2,3–Dihydrofuran as an Approach to Novel Imidazo[1,2–a]pyridine C–Nucleosides." *Tetrahedron Letters*.(1996) 37 (35):6275–6278.

Gudmundsson et al., "The Condensation of 2,6–Dichlororimidazo[1,2–a]Pyridine with Ribonolactone Gives a Novel Imidazo[1,2–a]pyridine C–nucleoside with an Unexpected Site of Ribosylation." *Tetrahedron Letters* (1996) 37 (14):2365–2368.

Herdewijn, P et al., "Synthesis of Nucleosides Fluorinated in the Sugar Moiety. The Application of Diethylaminosulfur Trifluoride to the Synthesis of Fluorinated Nucleosides." *Nucleosides and Nucleotides* (1989), 8, 65–96 and references therein.

Howell, H. G. et al., "Antiviral Nucleosides. A Stereospecific, Total Synthesis of 2'–Fluoro–2'–deoxy–$\beta$–D–arabinofuranosyl Nucleosides." *J. Org. Chem.* (1988), 53, 85–88.

Krezeminski, J. et al., Synthesis of 9–(2–Deoxy–2–fluoro–$\beta$–D–arabinofuranosyl)hypoxanthine. The First Direct Introduction of a 2'$\beta$–Fluoro Substituent in Preformed Purine Nucleosides. Studies Directed Toward The Synthesis of 2'–Deoxy–2'–Substituted Arabinonucleosides. *Nucleosides and Nucleotides*. (1991), 19, 781–798.

Montgomery, J. A. et al., "9–(2–Deoxy–2–fluoro–$\beta$–D–arabinofuranosyl)guanine: A Metabolically Stable Cytotoxic Analogue of 2'–Deoxyguanosine." *J. Med. Chem.* (1986), 29, 2389–2392.

Pankiewicz, K. W. et al., "A Synthesis of 9–(2–Deoxy–2–fluoro–$\beta$–D–arabinofuranosyl)adenine and Hypoxanthine. An Effect of C3'–Endo to C2'–Endo Conformational Shift on the Reaction Course of 2 '–Hydroxyl Group with DAST." *J. Org. Chem.* (1992), 57, 553–559.

Pankiewicz, K. W. et al., "A Synthesis of 2'–Fluoro–and 3'–Fluoro–Substituted Purine Nucleosides via a Direct Approach. In Nucleosides as Antitumor and Antiviral Agents"; Chu, C. K.; Baker, D. C., Eds.; Plenum Press: New York, (1993), pp. 55–71.

Prichard, M. N. et al,. *Antiviral Res.* (1991) vol. 15/4: 114 (abstract no. 133).

Reichman, U. et al., "A Practical Synthesis of 2–Deoxy–2–Fluoro–D–Arabinofuranose Derivaties." *Carbohydr. Res.* (1975), 42, 233–240.

Revenkar, R. G. and Townsend, L. B. "The Synthesis of 2–Chloro–1–($\beta$–D–ribofuranosyl–5,6–dimethylbenzimidazole and Certain Related Derivatives" (1968) *J. Heterocyclic Chem.* vol. 5:477–483.

Revenkar, R. G. and Townsend, L. B. "The Synthesis of 2–Chloro–1–($\beta$–D–ribofuranosyl)benzimidazole and Certain Related Derivatives"(1968) *J. Heterocyclic Chem.* vol. 5:615–620.

Saluja, S. et al. "Synthesis and antiviral activity of certain 2–substituted–5,6–dichlorobenzimidazole acyclic nucleosides." Poster#146. Division of Medicinal Chemistry, 204th American Chemical Society National Meeting, Washington, D.C., Aug. 23–28, (1992).

Shipman, C., Jr. et al. "Antiviral Activity of Arabinosyladenine and Arabinosylhypoxanthine in Herpes Simples Virus– Infected KB Cells:Selective Inhibition of Viral Deoxyribonucleic Acid Synthesis in Synchronized Suspension Cultures" *Antimicrobial Agents Chemotherapy* (1976), vol. 9 :120.

Shipman, C., Jr. et al., "A microtiter virus yield reduction assay for the evaluation of antiviral compounds against human cytomegalovirus and herpes simplex virus" *J. Virol. Methods.* (1990), vol. 28 :101–106.

Still, W. C. et al., "Rapid Chromatographic Techniques for Preparative Separation with Moderate Resolution." *J. Org. Chem.* (1978), 43, 2923–2925.

Sullivan, V. et al., "A Point Mutation in the Human Cytomegalovirus DNA Polymerase Gene Confers Resistance to Ganciclovir and Phosphonylmethoxyalkyl Derivatives" *Antimicrobial Agents and Chemotherapy* (1993),vol. 37, pp. 19–25.

Tamm, I., "Inhibition of Influenza and Mumps Virus Multiplication by 4,5,6,–(or 5,6,7,–) Trichloro–1–$\beta$–D–Ribofuranosyl–benzimidazole" *Science* (1954) vol. 120 :847–848).

Tann, C. H. et al., "Fluorocarbohydrates in Synthesis. An efficient Synthesis of 1–(2–Deoxy–2–fluoro–$\beta$–D–arabinofuranosyl)–5–iodouracil ($\beta$–FIAU) and 1–(2–Deoxy–2–fluoro–$\beta$–D–arabinofuranosyl)thymine ($\beta$–FMAU)." *J. Org. Chem.* (1985), 50,3644–3647.

Thiem, J. et al., "Synthesis and perkow Reaction of Uridine Derivatives." *Nucleosides and Nucleotides*.(1985), 4, 487.

Townsend and Revankar, "Benzimidazole Nucleosides, Nucleotides, and Related Derivatives" *Chem. Rev.* (1970), vol. 70, p. 389.

Townsend et al., "Design, Synthesis, and Antiviral Activity of Certain 2,5, 6–Trihalo–1–(B–D–ribofuranosyl)Benzimidazoles." *Journal of Medicinal Chemistry*.(1995) 38 (20) :4098–4105.

Turk, S. R. et al., "Pyrrolo[2,3–d]Pyrimidine Nucleosides as Inhibitors of Human Cytomegalovirus" *Antimicrobial Agents and Chemotherapy*(1987), vol. 31:544–550.

Wright, J. A. et al., "Nucleosides. LX. Fluorocarbohydrates. XXII. Synthesis of 2–deoxy–2–fluoro–D–arabinose and 9–(2–deoxy–2–fluoro–$\alpha$–and$\beta$arabinofuranosyl)adenines." *J. Org. Chem.* (1969), 34 2632–2636.

Zou, R. et al., "Design, synthesis and anitviral evaluation of some TCRB analogs modified on the benzene moiety," Poster #142. Division of Medicinal Chemistry, 204th American Chemical Society National Meeting, Washington, D. C., Aug. 23–28, (1992).

MODIFIED BENZIMIDAZOLE NUCLEOSIDES AS ANTIVIRAL AGENTS

This application claims priority benefit under 35 U.S.C. § 119(e) of U.S. Provisional Patent Application No. 60/010,463 filed 23 Jan. 1996.

FIELD OF THE INVENTION

This invention pertains to nucleoside analogs which have antiviral activity and improved metabolic stability. More specifically, this invention pertains to modified benzimidazole nucleosides, as exemplified by compounds such as benzimidazole nucleosides possessing a fluorinated sugar-like moiety (for example, a 2'-fluoro-furanosyl moiety or a 3'-fluoro-furanosyl moiety).

BACKGROUND OF THE INVENTION

Throughout this application, various publications, patents, and published patent applications are referred to by an identifying citation; full citations for these documents may be found at the end of the specification immediately preceding the claims. The disclosures of the publications, patents, and published patent specifications referenced in this application are hereby incorporated by reference into the present disclosure to more fully describe the state of the art to which this invention pertains.

Benzimidazole nucleosides are particularly attractive as potential antiviral agents because of their ability to avoid some major pathways of bioactive purine (bicyclic) nucleoside inactivation, e.g., deamination by adenosine deaminase and glycosidic bond cleavage by purine nucleoside phosphorylases. For example, current therapy for HCMV includes the use of drugs such as ganciclovir (also known as DHPG), foscarnet, and cidofovir. However, known benzimidazole nucleosides such as 5,6-dichloro-1-(β-D-ribofuranosyl)benzimidazole (DRB) have demonstrated only marginal levels of activity or generally unacceptable levels of cytotoxicity, or both, thereby greatly diminishing their usefulness in the treatment of viral infections. Recently, benzimidazole compounds, such as TCRB (2,5,6-trichloro-1-(2'-β-D-ribofuranosyl)benzimidazole) and 2-bromo-5,6-dichloro-1-(2'-β-D-ribofuranosyl)benzimidazole (BDCRB) have also been found to be useful against HCMV infections. See, for example, Townsend et al., 1993, 1994, 1995.

A number of benzimidazole nucleosides have been synthesized and tested for their antiviral activity and cytotoxicity in an effort to identify a compound with superior anti-human cytomegalovirus (HCMV) activity to ganciclovir and foscarnet. Antiviral activity of polysubstituted benzimidazoles such as 5,6-dichloro-1-(β-D-ribofuranosyl) benzimidazole (DRB) and some closely related derivatives have been previously described (Tamm, 1954). Their activity against specific viruses, such as RNA rhinovirus and DNA herpes simplex virus type 1 and type 2, also has been reported.

Several of the 5'-deoxyribosyl benzimidazole analogs, including 2,5,6-trichloro-1(β-D-ribofuranosyl) benzimidazole (TCRB) have shown very potent activity against HCMV and low cellular toxicity at concentrations inhibiting viral growth. Structural activity relationships of TCRB and heterocycle and carbohydrate modified derivatives have been reported. See, for example, Ravenkar et al., 1968a, 1968b; Townsend et al., March 1992; Zou et al., 1992; Saluja et al., 1992. These disclosures, however, do not disclose the structure or synthesis of the compounds which are the subject of this invention.

Some modifications of the heterocycle have given analogs that are significantly more active than TCRB. However, most of these analogs are also more cytotoxic than TCRB, resulting in compounds with a little improved therapeutic index. Attempts to modify the carbohydrate moiety, by replacing the ribose with arabinose, xylose or acyclic analogues have given compounds less active than TCRB. Somewhat surprisingly a 5'-deoxy derivative of TCRB, 2,5,6-trichloro-1(β-D-5'-deoxy-ribofuranosyl)benzimidazole was shown to be about 10 times more active than TCRB and have a better therapeutic index than TCRB.

Recent studies of the pharmacokinetics and metabolism of TCRB have revealed a drug half-life of about 0.6 hours in rats and 0.5–0.7 hours in monkeys (Good et al., 1994). The short half life may be associated with metabolic instability of the compound, for example, the cleavage of the sugar moiety from the benzimidazole.

SUMMARY OF THE INVENTION

One aspect of the present invention pertains to modified benzimidazole nucleosides possessing a fluorinated sugar-like moiety as described herein. In one embodiment, the fluorinated sugar-like moiety comprises a 2'-fluoro-furanosyl moiety or a 3'-fluoro-furanosyl moiety.

Another aspect of the present invention pertains to pharmaceutical compositions for treating viral infections which comprise a therapeutically effective amount of one or more of the modified benzimidazole nucleosides of the present invention, as described herein.

Yet another aspect of the present invention pertains to methods for treating viral infections in an animal patient comprising the step of administering a therapeutically effective amount of one or more of the modified benzimidazole nucleosides of the present invention, as described herein.

Still another aspect of the present invention pertains to methods for inhibiting viral (e.g., HCMV) proliferation in a virally infected cell comprising contacting the cell with an effective amount of one or more of the modified benzimidazole nucleosides of the present invention, as described herein, under suitable conditions such that viral proliferation is inhibited.

Still another aspect of the present invention pertains to methods for prophylactically treating a cell susceptible to viral (e.g., HCMV) infection, by contacting the cell with an effective amount of one or more of the modified benzimidazole nucleosides of the present invention, as described herein, under suitable conditions such that viral infection is prevented.

As will become apparent, preferred features and characteristics of one aspect of the invention are applicable to any other aspect of the invention.

DESCRIPTION OF THE PREFERRED EMBODIMENTS

Figure 1:
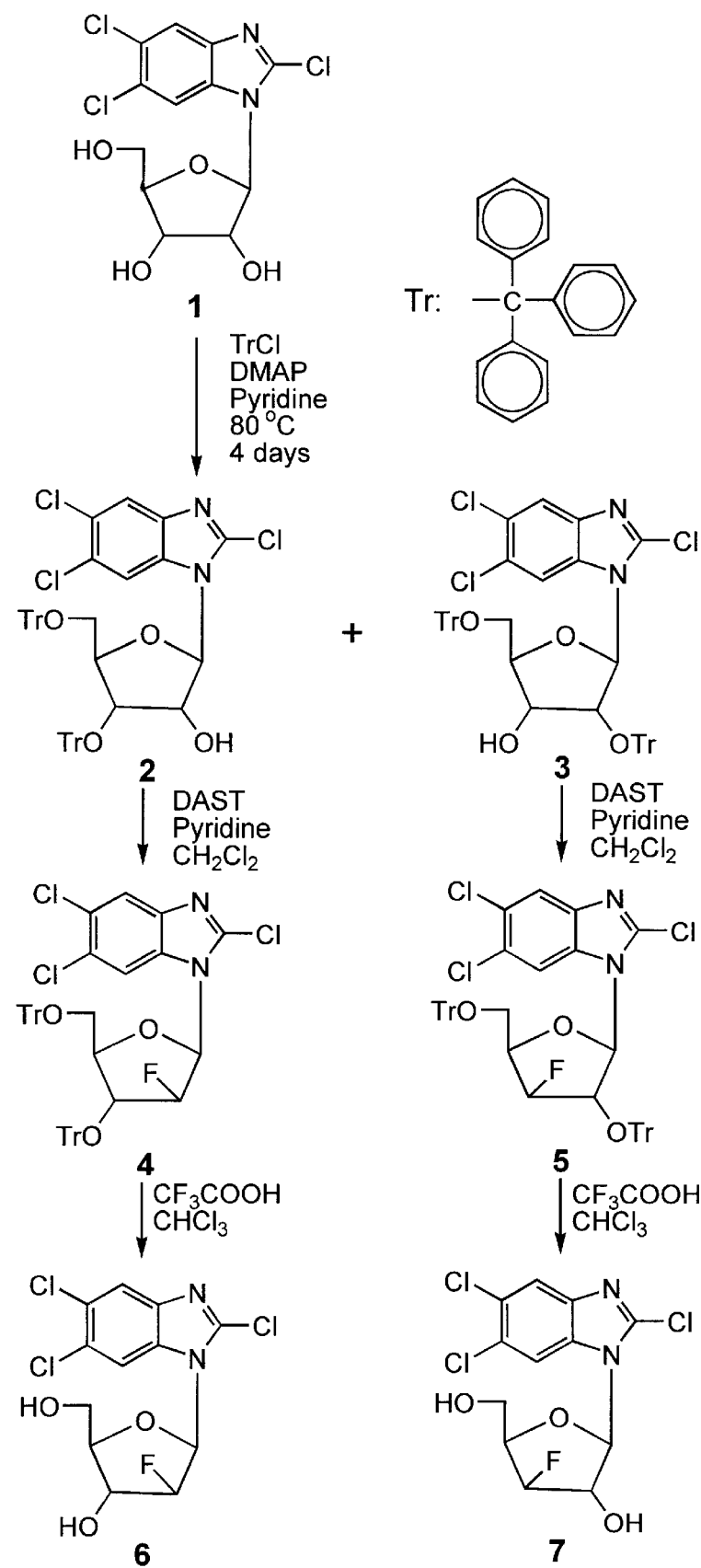
FIG. 1 is a flowchart illustrating a method for the chemical synthesis of modified benzimidazole nucleosides possessing a fluorinated sugar-like moiety.

A. Antiviral Compounds of the Present Invention

This invention pertains to modified benzimidazole nucleosides which have antiviral activity and low toxicity and which offer improved metabolic stability, and therefore, longer half-lives in vivo.

The compounds of the present invention may be described as "modified benzimidazole nucleosides," wherein the sugar-like moiety at the 1-position (i.e., $R^1$) of a substituted benzimidazoles has been derivatized, for example, to yield a fluorinated sugar-like moiety. The compounds of the present invention may be represented by the formula:

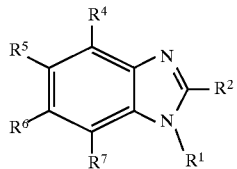

wherein $R^1$ is a fluorinated sugar-like moiety, and $R^2$, $R^4$, $R^5$, $R^6$ and $R^7$ are benzimidazole substituents. Examples of benzimidazole substituents include —H, halogens (e.g., —F, —Cl, —Br, —I), —$NO_2$, —$NR_2$ (where R is independently —H or an alkyl group having 1–6 carbon atoms), —OR (where R is —H or an alkyl group having 1–6 carbon atoms), —SR (where R is —H or a hydrocarbyl of 1–10 carbon atoms), and —$CF_3$.

In one embodiment, the compounds of the present invention may be represented by the above formula, wherein $R^1$ is a fluorinated sugar-like moiety; $R^2$ is —H, —F, —Cl, —Br, —I, or —$NR_2$ (where R is independently —H or an alkyl group having 1–6 carbon atoms); and $R^4$, $R^5$, $R^6$ and $R^7$ are independently —H, —F, —Cl, —Br, or —I.

In one embodiment, the compounds of the present invention may be represented by the above formula, wherein $R^1$ is a fluorinated sugar-like moiety; $R^2$ is —H, —F, —Cl, —Br, —I, or —$NR_2$ (where R is independently —H or an alkyl group having 1–6 carbon atoms); $R^5$ and $R^6$ are independently —H, —F, —Cl, —Br, or —I; and $R^4$ and $R^7$ are —H.

In another embodiment, the compounds of the present invention may be represented by the above formula, wherein $R^1$ is a fluorinated sugar-like moiety; $R^2$, $R^5$, and $R^6$ are independently —H, —F, —Cl, —Br, or —I; and $R^4$ and $R^7$ are —H.

In another embodiment, the compounds of the present invention may be represented by the above formula, wherein $R^1$ is a fluorinated sugar-like moiety; $R^2$ is —$NR_2$ (where R is independently —H or an alkyl group having 1–6 carbon atoms); $R^5$ and $R^6$ are independently —H, —F, —Cl, —Br, or —I; and $R^4$ and $R^7$ are —H.

In one embodiment, the compounds of the present invention may be represented by the above formula, wherein $R^1$ is a fluorinated sugar-like moiety; $R^2$, $R^5$, and $R^6$ are independently —H or —Cl; and $R^4$ and $R^7$ are —H.

The term "sugar-like moiety" as used herein relates to monosaccharide moieties. Preferred sugar-like moieties are in cyclic form, for example, derived from furanose (5-membered ring) or from pyranose (6-membered ring) forms, but more preferably from furanose forms. Examples of sugar-like moieties include threo-furanosyl (from threose, a four-carbon sugar); erythro-furanosyl (from erythrose, a four-carbon sugar); ribo-furanosyl (from ribose, a five-carbon sugar); ara-furanosyl (also often referred to as arabino-furanosyl; from arabinose, a five-carbon sugar); and xylo-furanosyl (from xylose, a five-carbon sugar). Examples of sugar-like moieties having further modifications include "deoxy", "keto", and "dehydro" derivatives, for example, 2'-deoxy-ribo-furanosyl; 3'-deoxy-ribo-furanosyl; 3'-keto-2'-deoxy-ribo-furanosyl; 2',5'-dihydrofuran-2'-yl; and 2'3'-dihydrofuran-2'-yl. Sugar-like moieties may be in any of their enantiomeric, diasteriomeric, or stereoisomeric forms, including, for example, D- or L-forms. The modified benzimidazole nucleosides of the present invention may be in any stereochemical configuration, including, for example, α- or β-anomeric form.

The term "fluorinated sugar-like moiety" as used herein relates to sugar-like moieties which have derivatized to include at least one fluorine atom (i.e., —F). For example, furanosyl (5-membered ring) groups derived from pentose (5-carbons) often have 2'-hydroxyl, 3'-hydroxyl, and 5'-hydroxyl groups. Fluorinated derivatives of such sugar-like moieties may be prepared, for example, by replacing one or more of the hydroxyl groups with fluoro groups. Examples of fluorinated sugar-like moieties include 2'-fluoro-furanosyl and 3'-fluoro-furanosyl. Examples of preferred fluorinated sugar-like moieties include 2'-fluoro-ara-furanosyl and 3'-fluoro-xylo-furanosyl.

As used herein, the term "fluorinated sugar-like moiety" also encompasses protected fluorinated sugar-like moieties. For example, fluorinated sugar-like moieties may possess one or more of 2'-hydroxyl, 3'-hydroxyl, and/or 5'-hydroxyl groups in a protected form, for example, as an ester (e.g., as an acetate, —O(C=O)$CH_3$), benzoate (i.e., —OC(=O)$C_6H_5$), or an ether (e.g., as a trityl ether, —OC($C_6H_5$)$_3$).

Throughout this application the disclosed and claimed compounds are identified by structure, name or by numerical designations. The compounds of this invention include, but are not limited to those examples shown below.

2,5,6-trichloro-1-(2'-fluoro-ara-furanosyl)benzimidazole (wherein $R^1$ is 2'-fluoro-ara-furanosyl; $R^2$ is —Cl; $R^4$ is —H; $R^5$ is —Cl; $R^6$ is —Cl; and $R^7$ is —H) (e.g., compound 6);

2,5,6-trichloro-1-(3'-fluoro-xylo-furanosyl)benzimidazole (wherein $R^1$ is 3'-fluoro-xylo-furanosyl; $R^2$ is —Cl; $R^4$ is —H; $R^5$ is —Cl; $R^6$ is —Cl; and $R^7$ is —H) (e.g., compound 7);

5,6-dichloro-1-(2'-fluoro-ribo-furanosyl)benzimidazole (wherein $R^1$ is 2'-fluoro-ribo-furanosyl; $R^2$ is —H; $R^4$ is —H; $R^5$ is —Cl; $R^6$ is —Cl; and $R^7$ is —H) (e.g., compound 15);

2-bromo-5,6-dichloro-1-(2'-fluoro-ribo-furanosyl) benzimidazole (wherein $R^1$ is 2'-fluoro-ribo-furanosyl; $R^2$ is —Br; $R^4$ is —H; $R^5$ is —Cl; $R^6$ is —Cl; and $R^7$ is —H) (e.g., compound 19);

2-isopropylamino-5,6-dichloro-1-(2'-fluoro-ribo-furanosyl)benzimidazole (wherein $R^1$ is 2'-fluoro-ribo-furanosyl; $R^2$ is —NH(CH($CH_3$)$_2$); $R^4$ is —H; $R^5$ is —Cl; $R^6$ is —Cl; and $R^7$ is —H) (e.g., compound 20);

The compounds of this invention are useful in the methods provided below or are useful as intermediates for the manufacture of other compounds of the present invention. It also should be understood, even though not always explicitly stated, that reference to any of the above compounds is to include pharmaceutically acceptable salts and operative combinations thereof.

B. Methods of Using the Antiviral Compounds of the Present Invention

As shown below, the compounds of this invention are potent antiviral drugs, and are particularly effective against HCMV and HSV-1, and as such, when combined with carriers, provide compositions for inhibiting viral reproduction and proliferation in vitro, ex vivo or in vivo. For example, the compounds can be combined with various liquid phase carriers, such as sterile or aqueous solutions, pharmaceutically acceptable carriers as defined below.

The compounds of this invention can be combined with other antiviral drugs to provide an operative combination. "Operative combination" is intended to include any chemically compatible combination of a compound of this inventive group with other compounds of the inventive group or other compounds outside the inventive group (such as ganciclovir, AZT, and focarnet), as long as the combination does not eliminate the antiviral activity of the compound of this inventive group.

The compounds of the invention could be used to treat HCMV and HSV-1 infections in AIDS patients already receiving the antiviral drug zidovudine (AZT). Combination therapies with AZT may provide the advantage of less toxicity over the combination of ganciclovir with AZT. The combination of the compounds of this invention with AZT may produce less cytotoxicity (i.e. antagonism) in cultured human cells than either agent used alone. In contrast, combination of ganciclovir with AZT may produce greater cytotoxicity in human cells than the use of either of these drugs alone.

This invention also provides a method of reducing or inhibiting HCMV or HSV-1 reproduction and proliferation in an HCMV or HSV-1 infected cell or population of cells by contacting the cell or population with an effective amount of a compound of this invention and under suitable conditions, such that viral reproduction and proliferation is inhibited. One of skill in the art can easily determine when HCMV or HSV-1 reproduction and proliferation has been reduced or inhibited by noting a reduction in viral titer or an increase of survival of the infected cells as compared to untreated, infected cells. Methods of assaying viral titer are well known to those of skill in the art and are exemplified below. It should be readily understood that by inhibiting and reducing viral replication and proliferation, viral infectivity also is inhibited and reduced and the cells are suitably treated for HCMV or HSV-1 infection.

For the purposes of this invention, a "cell" is intended to include, but not be limited to a mammalian cell, e.g., a mouse cell, a rat cell, a woodchuck cell, a simian cell, or a human cell. Viruses which are effectively treated by the compounds, compositions and methods of this invention include DNA and RNA viruses, particularly herpes viruses. Examples of herpes viruses, or herpesviridae, are herpes simplex virus 1 (HSV-1), herpes simplex virus 2 (HSV-2), varicella-zoster virus (VZV), Epstein-Barr virus (EBV), human cytomegalovirus (HCMV), human herpes virus 6 (HHV-6), human herpes virus 7 (HHV-7), and human herpes virus 8 (HHV-8). The compounds of the present invention are particularly useful in the treatment of HCMV and HSV-1 infections.

Effective amounts are easily determined by those of skill in the art and will vary with the cell, virus being effected and the purpose of the treatment. For example, when utilizing the drug in cell culture, it is important that the amount of drug not be cytotoxic to the cells.

"Suitable conditions" include in vitro, ex vivo or in vivo. When the method is practiced in vitro, contacting may be effected by incubating the cells with an effective antiviral amount of the compound, effective to inhibit viral reproduction and proliferation in the cell or culture of cells. The compound can be added directly to the culture media or combined with a carrier prior to addition to the cells. In vitro, the method is particularly useful for inhibiting viral reproduction, proliferation and therefore infection in laboratory cell cultures. Ex vivo, the compounds are useful to inhibit viral reproduction and proliferation in blood and plasma prior to reintroduction into a patient.

The use of the compounds and methods in vitro also provides a powerful bioassay to screen for novel drugs or compounds which provide similar or enhanced antiviral activity. Using the methods set forth below, the drug to be tested is assayed under the same conditions as a compound of this invention. Antiviral and cytotoxicity of the test drug can then be compared to a compound of this inventive group.

Although the compounds are shown below to be particularly effective against HCMV and HSV-1, one of skill in the art can easily determine other viruses effectively treated with the compounds of this invention by use of methods described herein and others well known to those of skill in the art. Other viruses contemplated to be treated within the scope of the present invention include, but are not limited to: human immunodeficiency virus (HIV) and hepatitis viruses.

When the method is practiced in vivo in a subject such as a human patient, the compound can be added to a pharmaceutically acceptable carrier and systemically or topically administered to the subject, such as a human patient or a mammal such as a mouse, a rat, a woodchuck, or a simian.

The compositions also can be administered to subjects or individuals susceptible to or at risk of a viral infection, such as HCMV or HSV-1 infection. Thus, this invention also provides a prophylactic method of inhibiting viral replication, proliferation and/or viral infection in a subject by administering to a subject a prophylactically effective amount of the compound or composition under suitable conditions such that viral replication, proliferation or infection is inhibited. A "prophylactically effective amount" is an amount which inhibits viral infection, reproduction and proliferation in a subject challenged with the virus without toxicity to the cells and subject being treated.

It should be understood that by preventing or inhibiting viral proliferation, infection and replication in a subject or individual, the compositions and methods of this invention also provide methods for treating, preventing or ameliorating the symptoms or disorders associated with the viral infection, such as inclusion disease, blindness, mononucleosis, restenosis (HCMV); chickenpox, shingles (varicella-zoster virus); infectious mononucleosis, glandular, fever, and Burkittis lymphoma (Epstein-Barr virus); cold sores (herpes simplex virus 1); genital herpes (herpes simplex virus 2); roseola infantum (human herpes virus 6, human herpes virus 7); kaposi sarcoma (human herpes virus 8). Thus, this invention also provides methods of ameliorating, preventing, or treating disorders or symptoms associated with viral infection, e.g., HCMV or HSV-1 infection, e.g., restenosis, opportunistic infections (such as retinal infections, gastrointestinal infections, pneumonia, CNS infections) and in utero infections, by administering to the subject an effective amount of a compound of this invention under suitable conditions such that the disorder or symptom is ameliorated, prevented, or treated.

Administration in vivo can be effected in one dose, continuously or intermittently throughout the course of treatment. Methods of determining the most effective means and dosage of administration are well known to those of skill in the art and will vary with the composition used for therapy, the target virus, the purpose of the therapy, the target cell being treated, and the subject being treated. Single or multiple administrations can be carried out with the dose level and pattern being selected by the treating physician. Suitable dosage formulations and methods of administering the compounds can be found below.

The fluorinated benzimidazole nucleosides of the present invention all exhibit antiviral activity against HCMV and HSV-1, many with acceptable cytotoxicity. It will be appreciated that compounds of the present invention which exhibit relatively high antiviral activity versus cytotoxicity, i.e. good selectivity, are preferred. It will also be appreciated that antiviral treatment in accordance with the present invention encompasses the treatment of viral infections, as well as prophylactic treatment which may be desired in certain situations, e.g in immunocompromised patients, such as bone marrow and organ transplant patients as well as patients harboring HIV who are particularly susceptible to HCMV or HSV-1 infection.

The compounds and compositions of the present invention can be used in the manufacture of medicaments and in antiviral treatment of humans and other animals by administration in accordance with conventional procedures, such as an active ingredient in pharmaceutical compositions. The compounds of the invention can be provided as pharmaceutically acceptable formulations and/or "prodrugs," including but not limited to esters, especially carboxylic acid esters (preferably $C_1$ to $C_{20}$), such as 5'-acetyl and 2',3',5'-triacetyl prodrugs and pharmaceutical salts such as thiolate, citrate and acetate salts.

The pharmaceutical compositions can be administered topically, orally, intranasally, parenterally or by inhalation therapy, and may take the form of tablets, lozenges, granules, capsules, pills, ampoules, suppositories or aerosol form. They may also take the form of ointments, gels, pastes, creams, sprays, lotions, suspensions, solutions and emulsions of the active ingredient in aqueous or nonaqueous diluents, syrups, granulates or powders. In addition to a compound of the present invention, the pharmaceutical compositions can also contain other pharmaceutically active compounds or a plurality of compounds of the invention.

More particularly, a compound of the formula of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, the virus being treated and the nature of the infection.

In general, a suitable dose for each of the above-named viral infections, e.g., HCMV and HSV-1, is in the range of about 0.1 to about 250 mg per kilogram body weight of the recipient per day, preferably in the range of about 1 to about 100 mg per kilogram body weight per day and most preferably in the range of about 5 to about 20 mg per kilogram body weight per day. Unless otherwise indicated, all weights of active ingredient are calculated as the parent compound of the formula of the present invention for salts or esters thereof, the weights would be increased proportionately. The desired dose is preferably presented as two, three, four, five, six or more sub-doses administered at appropriate intervals throughout the day. These sub-doses may be administered in unit dosage forms, for example, containing about 10 to about 1000 mg, preferably about 20 to about 500 mg, and most preferably about 100 to about 400 mg of active ingredient per unit dosage form. It will be appreciated that appropriate dosages of the compounds and compositions of the invention may depend on the type and severity of the viral infection and can vary from patient to patient. Determining the optimal dosage will generally involve the balancing of the level of therapeutic benefit against any risk or deleterious side effects of the antiviral treatments of the present invention.

Ideally, the active ingredient should be administered to achieve peak plasma concentrations of the active compound of from about 2 $\mu$M to about 100 $\mu$M, preferably about 5 $\mu$M to about 70 $\mu$M, most preferably about 1 to about 50 $\mu$M. This may be achieved, for example, by the intravenous injection of about 0.1 to about 5% solution of the active ingredient, optionally in saline, or orally administered, for example, as a tablet, capsule or syrup containing about 0.1 to about 250 mg per kilogram of the active ingredient. Desirable blood levels may be maintained by a continuous infusion to provide about 0.01 to about 5.0 mg/kg/hour or by intermittent infusions containing about 0.4 to about 15 mg per kilogram of the active ingredient. The use of operative combinations is contemplated to provide therapeutic combinations requiring a lower total dosage of each component antiviral agent than may be required when each individual therapeutic compound or drug is used alone, thereby reducing adverse effects, e.g., cytotoxicity.

While it is possible for the active ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For infections of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the active ingredient may be employed with either a paraffinic or a water-miscible ointment base. Alternatively, the active ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulfoxide and related analogues.

The oily phase of the emulsions of this invention may be constituted from known ingredients in an known manner. While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulation in a concentration of about 0.5 to about 20%, advantageously about 0.5 to about 10% particularly about 1.5% w/w.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an active ingredient.

It should be understood that in addition to the ingredients particularly mentioned above, the formulations of this invention may include other agents conventional in the art having regard to the type of formulation in question, for example, those suitable of oral administration may include such further agents as sweeteners, thickeners and flavoring agents.

Compounds of the formula of the present invention may also be presented for the use in the form of veterinary formulations, which may be prepared, for example, by methods that are conventional in the art.

C. Preparation of the Modified Sugar Substituted Benzimidazoles

General Chemical Procedures

Melting points were taken on a Thomas-Hoover Unimelt apparatus and are uncorrected. Nuclear magnetic resonance (NMR) spectra were obtained at 360 or 300 MHz with Bruker WP 360 SY or Bruker 300 SY. Elemental analysis were performed by the Analytical Laboratory of the Chemistry Department, University of Michigan. Mass spectra were performed by the Mass Spectral Laboratory of the Chemistry Department, University of Michigan. Flash column chromatography was performed using silica gel 60 230–400 mesh (ICN) and the technique described by Still et al. (Still et al., 1978). Thin layer chromatography (TLC) was performed on prescored Silica gel GHLF plates (Analtech, Newark, Del., U.S.A.). Compounds were visualized by illumination under UV light (254 nm) or by spraying with 20% methanolic sulfuric acid followed by charring on a hot plate. Evaporations were carried out under reduced pressure (water aspirator) with water bath temperatures below 40° C. unless otherwise specified.

Fluorinated nucleosides have commonly been synthesized by either of two different routes. One route introduces the fluorine into a suitably protected nucleoside while the other route condenses (e.g., chemically or enzymatically) a heterocycle with a fluorinated sugar derivative. Both of these strategies were investigated.

Fluorination of Benzimidazole Nucleoside

One method for the synthesis of a modified benzimidazole nucleoside is illustrated in FIG. 1. In this method, a benzimidazole nucleoside, such as 2,5,6-trichloro-1-furanosyl-benzimidazole was reacted with trityl chloride (i.e., TrCl), dimethylaminopyridine (DMAP) and pyridine at 80° C. for 4 days to yield a mixture of the 2',5'-ditritylated and 3',5'-ditritylated compounds. The 2',5'-ditritylated compound was reacted with DAST (i.e., SF$_3$NEt$_2$) in pyridine and dichloromethane (i.e., CH$_2$Cl$_2$), and subsequently reacted with trifluoroacetic acid (i.e., CF$_3$COOH) to yield the 3'-deoxy-3'-fluoro compound, 2,5,6-trichloro-1-(3'-deoxy-3'-fluoro-furanosyl)benzimidazole. In one embodiment, the compound is 2,5,6-trichloro-1-(3'-deoxy-3'-fluoro-β-xylo-furanosyl)benzimidazole, compound 7. Similarly, the 3',5'-ditritylated compound was reacted with DAST (i.e., SF$_3$NEt$_2$) in pyridine and dichloromethane (i.e., CH$_2$Cl$_2$), and subsequently reacted with trifluoroacetic acid (i.e., CF$_3$COOH) to yield the 2'-deoxy-2'-fluoro compound, 2,5,6-trichloro-1-(2'-deoxy-2'-fluoro-furanosyl)benzimidazole. In one embodiment, the compound is 2,5,6-trichloro-1-(2'-deoxy-2'-fluoro-β-ara-furanosyl)benzimidazole, compound 6.

The glycosylation of several purines with 2'-deoxy-2'-fluoro-arabinofuranosyl derivatives has examined (Chu et al., 1989; Pankiewicz et al., 1992). The fluorination of a suitably protected derivative of compound 1 with dialkylamino sulfur trifluoride (DAST) was investigated, as described herein. While DAST has been reported to be an efficient fluorinating reagent for several nucleosides, it is well known that the conformation of the protected furanose moiety is crucial for obtaining the desired attack of the weakly nucleophilic fluorine from the β-side (Krezeminski et al., 1991; Pankiewicz et al., 1993). For a displacement of a leaving group at the 2'-position it is important that the furanose ring assumes a conformation unfavorable for transelimination. Such a conformation can be induced by using bulky protecting groups at C-5' and C-3' (Theim et al., 1985).

2,5,6-trichloro-1-(3,5-di-O-trityl-β-D-ribofuranosyl) benzimidazole (compound 2) was synthesized using reaction conditions similar to those described in the literature (Blank et al., 1970). Tritylation of compound 1 using TrCl and DMAP in pyridine at 80° C. for 4 days gave a mixture of the ditrityl derivatives 2,5,6-trichloro-1-(3,5-di-O-trityl-β-D-ribofuranosyl)benzimidazole (compound 2) and 2,5,6-trichloro-1-(2,5-di-O-trityl-β-D-ribofuranosyl) benzimidazole (compound 3) in a combined 38% yield. Attempts to improve the yield by increasing the reaction time, reaction temperature or using bases other than DMAP to catalyze the reaction were unsuccessful. The di-O-trityl derivatives, compounds 2 and 3, could not be separated by flash column chromatography, but were separable by thin layer chromatography (EtOAc/hexane: 1:2, three to four submersions). These compounds were more conveniently separated by fractional crystallization from diethyl ether to give a 1:3 ratio of compounds 3 and 2. Substantiation for the assignment of compound 3 as the 2',5'-di-O-trityl derivative and compound 2 as the 3',5'-di-O-trityl derivative was based on homonuclear decoupling experiments.

While the desired 3',5'-di-O-trityl derivative, compound 2, was only obtained in 10% yield from compound 1, the isomeric 2',5'-ditrityl derivative, compound 3, was obtained in a 30% yield. The fluorination of compound 3 using DAST and pyridine in CH$_2$Cl$_2$ gave 2,5,6-trichloro-1-(2,5-di-O-trityl-3-deoxy-3-fluoro-β-D-xylofuranosyl)benzimidazole (compound 5) in a 71% yield. The fluorination of compound 2 using the same conditions gave 2,5,6-trichloro-1-(3,5-di-O-trityl-2-deoxy-2-fluoro-β-D-arabinofuranosyl) benzimidazole (compound 4) in a 63% yield. Both compounds 4 and 5 were deprotected using 10% CF$_3$COOH in CHCl$_3$ to give good yields of the deprotected nucleosides 2,5,6-trichloro-1-(2-deoxy-2-fluoro-β-D-arabinofuranosyl) benzimidazole (compound 6) and 2,5,6-trichloro-1-(3-deoxy-3-fluoro-β-D-xylofuranosyl)benzimidazole (compound 7), respectively.

The fluoro derivatives 6 and 7 are the β-arabino-furanosyl and β-xylo-furanosyl derivatives, respectively, as they were synthesized from the pre-formed β-ribofuranosyl nucleoside, compound 1, using DAST. These DAST fluorinations are known to replace a hydroxyl group with fluorine with an inversion of configuration (Herdewijn et al., 1989). Further support for the assignments of compounds 6 and 7 as the β-arabinofuranosyl and β-xylofuranosyl derivatives, respectively, stems from the fact that both show long range coupling between the C$_7$-H and F: this coupling is slightly larger for compound 6 (J=1.9 Hz) than for compound 7 (J=1.7 Hz). This indicates that the fluorine and the heterocycle are on the same face of the furanose ring. Finally for the arabinose derivative compound 6, the coupling between the 1'-H and the F is 17.7 Hz: this coupling is indicative of a vicinal trans relation between the 1'-H and F (Wright et al., 1969).

Compounds 2 and 3

2,5,6-trichloro-1-(3,5-di-O-trityl-β-D-ribofuranosyl) benzimidazole (2) and 2,5,6-Trichloro-1-(2,5-di-O-trityl-β-D-ribofuranosyl)benzimidazole (3).

A mixture of compound 1 (5.0 g, 0.014 mole), DMAP (1.25 g, 0.014 mole), and TrCl (12.0 g, 0.043 mole) in dry pyridine (100 mL) was heated at 80° C. for 3 days. Additional amounts of TrCl (12.0 g, 0.043 mole) were added on the 2nd and 3rd day. After 3 days the reaction was quenched with MeOH (60 mL). The reaction mixture was concentrated under reduced pressure and coevaporated with toluene (3×100 mL). The residue obtained was stirred in toluene (150 mL), filtered and the filtrate evaporated to dryness. The resulting yellow foam was purified by flash chromatography (toluene 0.5 L, then toluene/EtOAc 20:1, 5 cm×20 cm) to give, after combining fractions containing ditrityl compounds and removal of the solvent under reduced pressure a mixture of compounds 2 and 3 (4.5 g, 38%). Recrystallization from EtOEt gave mostly compound 3 while the filtrate was enriched in compound 2. Compound 3 could be purified to homogeneity by two further recrystallizations from EtOEt to give 3.0 g (25%) of compound 3 as white crystals. The filtrate, which contained mostly compound 2, was evaporated to dryness and subsequently purified by recrystallization from EtOAc/hexane to give 1.0 g (8.4%) of pure compound 2 as white crystals.

Compound 2: mp 174°–175° C.; $R_f$ 0.19 (toluene/EtOAc 20:1); $R_f$ 0.62 (EtOAc/hexane 1:2); $^1$H-NMR (300 MHz, DMSO-$d_6$):δ 8.06 (s, 1H), 8.02 (s, 1H), 7.13–7.42 (m, 30H, trityl), 6.24 (d, 1H, 2'-OH, $J_{2',OH}$=6.2 Hz), 6.18 (d, 1H, 1'-H, $J_{1',2'}$=8.3 Hz), 4.76 (m, 1H, 2'-H, becomes q on $D_2O$ wash with $J_{1',2'}$=7.9 Hz, $J_{2',3'}$=5.3 Hz), 4.23 (d, 1H, 3'-H, $J_{2',3'}$=5,4 Hz), 2.93 (m, 1H, 4'-H), 2.86 (dm, 1H, 5'-H), 2.64 (dm, 1H, 5'-H). Anal. Calcd. for $C_{50}H_{39}Cl_3N_2O_4$: C, 71.65, H, 4.69, N, 3.34; found C, 71.50, H, 4.85, N, 3.24.

Compound 3: mp 193°–195° C.; $R_f$ 0.19 (toluene/EtOAc 20:1); $R_f$ 0.62 (EtOAc/hexane 1:2); $^1$H-NMR (300 MHz, DMSO-$d_6$):δ 7.93 (s, 1H), 7.54 (s, 1H), 7.01–7.41 (m, 30H, trityl), 6.22 (d, 1H, 1'-H, $J_{1',2'}$=8.4 Hz), 5.39 (d, 1H, 3'-OH, $J_{3',OH}$=6.0 Hz), 4.50 (dd, 1H, 2'-H, $J_{1',2'}$=8.4 Hz, $J_{2',3'}$=4.4 Hz), 4.09 (m, 1H, 4'-H), 3.58 (t, 1H, 3'-H, $J_{3',OH}$=6.0 Hz, $J_{2',3'}$=4.4 Hz: becomes a doublet on $D_2O$ wash with $J_{2',3'}$=4.4 Hz), 3.04 (dd, 1H, 5'-H), 3.18 (dd, 1H, 5'-H). Anal. Calcd. for $C_{50}H_{39}Cl_3N_2O_4 \cdot \frac{1}{2}$ $H_2O$: C, 70.88, H, 4.76, H, 3.31; found C, 70.93, H, 4.80, N, 3.31.

Compound 4

2,5,6-Trichloro-1-(3,5-di-O-trityl-2-deoxy-2-fluoro-β-D-arabinofuranosyl)benzimidazole (4).

The 3',5'-di-O-trityl compound, compound 2 (0.3 g, 0.36 mmol), was dissolved in dry $CH_2Cl_2$ (10 mL). To this solution was added pyridine (0.3 mL, 3.6 mmol) and DAST (0.24 mL, 1.8 mmol) and the reaction stirred at room temperature for 24 hr. Additional $CH_2Cl_2$ (200 mL) was added to the reaction mixture and the mixture extracted with saturated $NaHCO_3$ (100 mL) and washed with water (100 mL). The organic phase was dried over magnesium sulfate, filtered and the solvent removed in vacuo. The resulting syrup was purified by flash chromatography (EtOAc/hexane 1:2, 2 cm×15 cm), fractions containing product were pooled and solvent removed in vacuo to give, after recrystallization from EtOH, 0.20 g (67%) of compound 4 as a white solid.

Compound 4: mp 145° C.; $R_f$ 0.57 (EtOAc/hexane 1:2); $^1$H-NMR (360 MHz, CDCl$_3$):δ 7.65 (d, 1H, $C_7$-H, J=3.7 Hz, long range coupling to F), 7.62 (s, 1H, $C_4$-H), 7.19–7.45 (m, 30H, Tr), 6.10 (dd, 1H, 1'-H, $J_{1',F}$=24.7Hz, $J_{1',2'}$=2.3 Hz), 4.57 (1H, 4'-H), 4.28 (dm, 1H, 3'-H, $J_{3',F}$=15.9 Hz), 3.60 (dd, 1H, 2'-H, $J_{2',F}$=50.3 Hz, $J_{1',2'}$=2.3 Hz), 3.50 (m, 1H, 5'-H), 3.27 (m, 1H, 5'-H). HRMS m/z calcd. for $C_{50}H_{38}Cl_3FN_2O_3$ 838.1932, found 838.1949. Anal. Calcd. for $C_{50}H_{38}Cl_3FN_2O_3$: C, 71.47, H, 4.56, N, 3.33; found C, 71.15, H, 4.72, N, 3.37.

Compound 5

2,5,6-Trichloro-1-(2,5-di-O-trityl-3-deoxy-3-fluoro-β-D-xylofuranosyl)benzimidazole (5).

The 2',5'-ditrityl compound, compound 3 (1.2 g, 1.44 mmol), was dissolved in dry $CH_2Cl_2$ (30 mL). To this solution was added pyridine (1.1 mL, 14.4 mmol) and DAST (1.0 mL, 7.2 mmol) and the reaction mixture was stirred at room temperature for 24 hr. Additional $CH_2Cl_2$ (200 mL) was added to the reaction mixture and the mixture extracted with saturated $NaHCO_3$ (100 mL) and washed with water (100 mL). The organic phase was then dried over magnesium sulfate, filtered and the solvent removed in vacuo. The resulting syrup was purified by flash chromatography (EtOAc/hexane 1:2, 4 cm×15 cm) and fractions containing product were combined and the solvent removed under reduced pressure to give, after recrystallization from EtOH, 0.85 g (70%) of compound 5 as a white solid.

Compound 5: mp>240° C. (decomposes); $R_f$ 0.6 (EtOAc/hexane 1:2): $^1$H-NMR (300 MHz, CDCl$_3$):δ 7.73 (s, 1H), 7.17–7.40 (m, 31H, $C_4$-H and trityl), 6.17 (d, 1H, 1'-H, $J_{1',2'}$=4.5 Hz), 4.54 (dd, 1H, 2'-H, $J_{1',2'}$=4.5 Hz, $J_{2',F}$=20.9 Hz), 4.14 (dm, 1H, 4'-H, $J_{4',F}$=31.4 Hz), 3.99 (dd, 1H, 3'-H, $J_{3',F}$=50.6 Hz, $J_{3',4'}$=2.1 Hz), 3.50 (m, 1H, 5'-H), 3.27 (m, 1H, 5'-H). HRMS m/z calcd. for $C_{50}H_{38}Cl_3FN_2O_3$ 838.1924, found 838.1957. Anal. Calcd. for $C_{50}H_{38}Cl_3FN_2O_3 \cdot \frac{1}{2}$ $H_2O$: C, 70.72, H, 4.63, N, 7.88; found C, 70.82, H, 4.77, N, 3.35.

Compound 6

2,5,6-Trichloro-1-(2-deoxy-2-fluoro-β-D-arabinofuranosyl)benzimidazole (6)

Compound 4 (0.10 g, 0.12 mmol) was dissolved in 10% $CF_3COOH$ in CHCl$_3$ (10 mL) and stirred at room temperature in a stoppered flask for 60 min. The reaction mixture was evaporated to dryness in vacuo, the oily residue was purified by flash chromatography (EtOAc/hexane 5:1, 2 cm×15 cm), appropriate fractions pooled, solvent removed in vacuo and the white residue crystallized from MeOH/$H_2O$ to give 25 mg (60%) of compound 6 as white crystals.

Compound 6: mp 223° C.; $R_f$ 0.43 (EtOAc/hexane 5:1); $^1$H-NMR (360 MHz, DMSO-$d_6$):δ 8.29 (d, 1H, $C_7$-H, J=1.9 Hz, long range coupled to F), 7.93 (s, 1H, $C_4$-H), 6.44 (dd, 1H, 1'-H, $J_{1',F}$=17.7 Hz, $J_{1',2'}$=4.5 Hz), 6.02 (d, 1H, 3'-OH, $D_2O$ exchangeable), 5.3–5.35 (m, 1.5H, 5'-OH and 0.5 of 2'-H, 5'-OH $D_2O$ exchangeable), 5.25 (dm, 0.5H, 2'-H, $J_{2',F}$=53.2 Hz, $J_{2',3'}$=2.7 Hz), 4.42 (dm, 1H, 3'-H, becomes ddd on $D_2O$ wash with $J_{3',F}$=24.2 Hz, $J_{2',3'}$=2.7 Hz and $J_{3',4'}$=5.9 Hz), 3.71–3.86 (m, 3H, 4'-H and 5'-H); $^{13}$C-NMR (90 Mhz, DMSO-$d_6$):δ 140.81, 140.60, 134.07, 126.07, 125.68, 119.88, 115.61, 97.38 (2'C, $J_{2'C,F}$=192.5 Hz), 84.98 (1'C, $J_{1'C,F}$=17.4 Hz), 82.89 (4'C), 73.25 (3'C, $J_{2'C,F}$=24.4 Hz), 59.05 (5'C, $J_{5'C,F}$=9.9 Hz); HRMS m/z calcd. for $C_{12}H_{10}Cl_3FN_2O_3$ 353.9741, found 353.9735. Anal. Calcd. for $C_{12}H_{10}Cl_3FN_2O_3$: C, 40.53, H, 2.83, N, 7.88; found C, 40.55, H, 2.94, N, 7.48.

Compound 7

2,5,6-Trichloro-1-(3-deoxy-3-fluoro-β-D-xylofuranosyl)benzimidazole (7)

Compound 5 (0.28 g, 0.32 mmol) was dissolved in 10% $CF_3COOH$ in CHCl$_3$ (20 mL) and stirred at room temperature in a stoppered flask for 45 min. The reaction mixture was evaporated to dryness in vacuo, the oily residue was purified by flash chromatography (EtOAc/hexane 5:1, 2 cm×15 cm), appropriate fractions pooled, evaporated to dryness and crystallized from MeOH/$H_2O$ to give 85 mg (74%) of compound 7 as white crystals.

Compound 7: mp 238° C.; $R_f$ 0.42 (EtOAc/hexane 5:1); $^1$H-NMR (300 MHz, DMSO-$d_6$):δ 8.01 (s, 1H, $C_4$-H), 7.93 (d, 1H, $C_7$-H, J=1.7 Hz, long range coupled to F), 6.29 (d, 1H, 2'-OH, $D_2O$ exchangeable), 5.91 (d, 1H, 1'-H, $J_{1',2'}$=4.6 Hz), 5.17 (dd, 1H, 3'-H, $J_{3',F}$=52.8 Hz), 5.14 (t, 1H, 5'-OH, $D_2O$ exchangeable), 4.63 (dm, 1H, 2'-H, $J_{2',F}$=22.6 Hz, becomes dd on $D_2O$ wash with $J_{2',F}$=22.6 Hz and $J_{1',2'}$=4.6 Hz), 4.30 (dm, 1H, 4'-H, $J_{4',F}$=28.5 Hz), 3.69–3.84 (m, 2H, 5'-H); $^{13}$C-NMR (90 MHz, DMSO-d$_6$):δ 141.80, 140.94, 132.19, 125.967, 120.40, 113.61, 113.53, 96.90 (3'C, J$_{3'C,F}$=184.1 Hz), 91.14 (1'C, J$_{1'C,F}$=4.6 Hz), 80.46 (4'C, J$_{4'C,F}$=19.8 Hz), 77.81 (2'C, J$_{2'C,F}$=26.89 Hz), 57.71 (5'C, J$_{5'C,F}$=9.96 Hz); HRMS m/z calcd. for C$_{12}$H$_{10}$Cl$_3$FN$_2$O$_3$ 353.9741, found 353.9747. Anal. Calcd. for C$_{12}$H$_{10}$Cl$_3$FN$_2$O$_3$: C, H, N. Anal. Calcd. for C$_{12}$H$_{10}$Cl$_3$FN$_2$O$_3$: C, 40.53, H 2.83 , N, 7.88; found C, 40.77, H, 2.88, N, 7.56.

Coupling of a Fluorinated Sugar with a Benzimidazole

Figure 2:
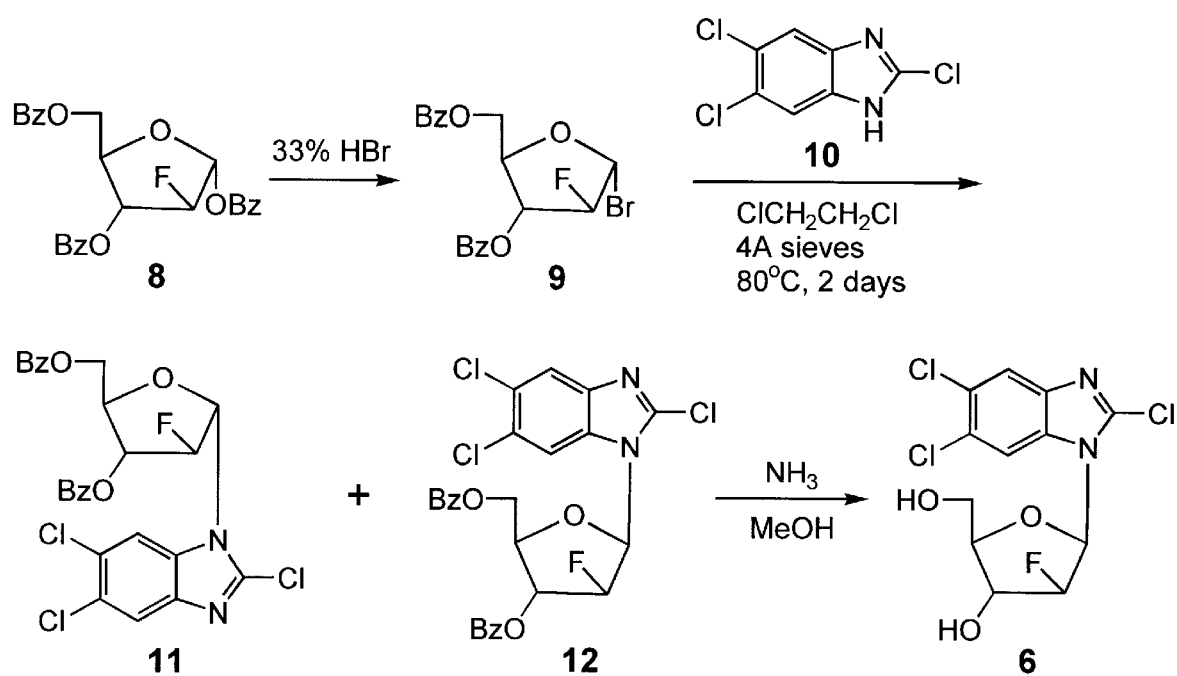
FIG. 2 is a flowchart illustrating another method for the chemical synthesis of modified benzimidazole nucleosides possessing a fluorinated sugar-like moiety.

Another method for the synthesis of a modified benzimidazole nucleoside is illustrated in FIG. 2. In this method, a fluorinated sugar-like compound is prepared and subsequently reacted with a benzimidazole to form the desired compound. For example, a furanose which is 2'-, 3'-, and 5'-protected with benzoyl groups (i.e., —OC(=O)C$_6$H$_5$) and 1'-protected with an acetate group (i.e., —OC(=O)CH$_3$) was converted to a 1'-deoxy-1'-bromo-2'-deoxy-2'-fluoro-3',5'-benzoyl-furanose (see Howell et al., 1995). This bromo-furanose was reacted with a benzimidazole, such as 2,5,6-trichlorobenzimidazole, in 1,2-dichloroethane (i.e., ClCH$_2$CH$_2$Cl) with 4 Å sieve at 80° C. for 2 days to yield a mixture of 2,5,6-trichloro-1-(2'-deoxy-2'-fluoro-3',5'-benzoyl-furanosyl)benzimidazole isomers. Subsequent deprotection by reaction with ammonia (i.e., NH$_3$) in methanol (i.e., CH$_3$OH) yielded the 2,5,6-trichloro-1-(2'-deoxy-2'-fluoro-furanosyl)benzimidazole. In one embodiment, the compound is 2,5,6-trichloro-1-(2'-deoxy-2'-fluoro-β-arafuranosyl)benzimidazole (compound 6).

The synthesis of 6 by the coupling of a fluorinated arabinofuranose compound (such as compounds 8 or 9) to a benzimidazole (such as 2,5,6-trichlorobenzimidazole, compound 6) was investigated. Initial attempts to use Vorbruggen conditions and attempts to glycosylate an alkali salt of compound 6 were unsuccessful. Compound 6 was successfully condensed with 1-bromo-3,5-di-O-benzoyl-2-deoxy-2-fluoro-α-D-arabinofuranose (compound 9; Tann et al., 1985; Howell et al., 1988) using conditions similar to those described by Montgomery et al. (Montgomery et al., 1986). Thus, condensation of compound 6 with compound 9 at 80° C. in dichloroethane in the presence of 4 Å molecular sieves gave the desired 2,5,6-trichloro-1-(3,5-di-O-benzoyl-2-deoxy-2-fluoro-β-D-arabinofuranosyl)benzimidazole (compound 12) and its α-isomer (compound 11). The assignment of compound 12 as the β-anomer and compound 11 as the α-anomer is based partially on their proton spectra. The coupling constant between the fluorine and the 1'-H is J$_{1',F}$=23.1 Hz for compound 17 indicating a vicinal trans relation of the proton to the fluorine. For compound 16 this coupling constant is J$_{1',F}$=17.4 Hz indicating a vicinal cis relation of the proton to the fluorine (Wright et al., 1969, Tann et al., 1985; Howell et al., 1988; Reichman et al., 1975). Further substantiation for the anomeric assignment stems from the fact that the C$_7$-H at 7.91 ppm in compound 16 is split by long range coupling to fluorine (the signal is a doublet, J=3.2 Hz due to coupling between C$_7$-H and F) which is not observed at C$_7$-H at 7.79 ppm for compound 17 (in this case the signal is a singlet).

Further investigation of the condensation conditions showed that the anomeric ratio was highly dependent on condensation conditions. The condensation conditions described above gave mostly the β anomer, compound 17 (α/β ratio: 1/5–1/10) in nonpolar solvents like dichloroethane and benzene. However, the α-anomer compound 16 (α/β ratio 5/1 –10/1) was the major product in more polar solvents such as acetonitrile and nitromethane. Yields were significantly better in apolar solvents such as dichloroethane (80% 8/1 β/α) than in polar solvents such as acetonitrile (9% 1/7 β/α).

Deprotection of compound 12 in methanolic ammonia gave a compound identical to the previously characterized compound 6. Thus, an alternative route for the synthesis of compound 6 had been developed, which gave compound 6 in approximately 50% yield from the heterocycle (compound 6) and bromo sugar (compound 15), as compared to the approximately 5% yield obtained using the previous method.

Compounds 11 and 12

2,5,6-Trichloro-1-(3,5-di-O-benzoyl-2-deoxy-2-fluoro-β-D-arabinofuranosyl)benzimidazole (12) and its α-isomer (11)

The 2-fluorosugar, compound 8 (1.20 g, 2.6 mmol; Tann et al., 1985) was dissolved in CH$_2$Cl$_2$ (10 mL) and then a 33% HBr in CH$_3$COOH solution was added (2.64 mL, 10.4 mmol). The reaction mixture was stirred in a stoppered flask for 6 hr. Additional CH$_2$Cl$_2$ (100 mL) was added to the reaction mixture and the organic phase was washed sequentially with ice cold saturated NaHCO$_3$ (100 mL) and ice cold water (100 mL). The CH$_2$Cl$_2$ solution was dried over magnesium sulfate, filtered and the solvent was removed under reduced pressure to give a colorless syrup of compound 9.

This syrup was dissolved in dry ClCH$_2$CH$_2$Cl (10 mL) and added to a previously prepared solution containing 2,5,6-trichlorobenzimidazole, compound 10 (0.6 g, 2.6 mmol) in ClCH$_2$CH$_2$Cl (10 mL) and activated 4 Å sieves. The resulting mixture was heated at 80° C. under an inert atmosphere for 2 days. Then CH$_2$Cl$_2$ (100 mL) and a saturated NaHCO$_3$ solution (100 mL) were added to the reaction mixture. The organic phase was separated and washed with water (100 mL), then dried over magnesium sulfate, filtered and the solvent was removed in vacuo. The resulting solid was purified by flash chromatography (EtOAc/hexane: 1:2, 4 cm×15 cm) with the fractions containing the faster moving nucleoside being pooled, concentrated to dryness and recrystallized from MeOH/H$_2$O and then from EtOH to give 0.12 g (8%) of compound 11 as white crystals. The fractions containing the slower moving nucleoside were contaminated with a small amount of compound 10. These contaminated fractions were pooled, concentrated to dryness and rechromatographed on a second column (5% MeOH in CHCl$_3$, 4 cm×15 cm) to give after pooling appropriate fractions and removing solvent under reduced pressure a white solid which after recrystallizations from MeOH/H$_2$O gave 1.0 g (72%) of compound 12.

Compound 11: mp 78°–80° C.; R$_f$ 0.60 (EtOAc/hexane 1:2); R$_f$ 0.9 (5% MeOH in CHCl$_3$); $^1$H-NMR (360 MHz, CDCl$_3$):δ 8.12 and 8.00 (2m, 4H), 7.79 (s, 1H), 7.72 (s, 1H), 7.24–7.63 (m, 6H, benzoyl), 6.64 (dd, 1H, 1'-H, J$_{1',2'}$=3.9 Hz, J$_{1',F}$=17.4 Hz), 5.82 (dd, 1H, 2'-H, J$_{2',F}$=18.7 Hz, J$_{2',3'}$=1.9 Hz), 5.63 (dm, 1H, 3'-H, J$_{3',F}$=49.3 Hz), 4.94 (m, 1H, 4'-H), 4.88 (dd, 1H, 5'-H), 4.67 (dd, 1H, 5'-H); HRMS m/z calcd. for C$_{26}$H$_{18}$Cl$_3$FN$_2$O$_5$ 562.0265 found 562.0276. Anal. Calcd. for C$_{26}$H$_{18}$Cl$_3$FN$_2$O$_5$: C, 55.39, H, 3.22, N, 4.97; found C, 55.74, H 3.23, N 4.87.

Compound 12: mp 88°–90° C.; R$_f$ 0.36 (EtOAc/hexane 1:2); R$_f$ 0.67 (5% MeOH in CHCl$_3$); $^1$H-NMR (360 MHz, CDCl$_3$):δ 8.07–8.18 (m, 4H), 7.91 (d, 1H, C$_7$-H, J=3.2 Hz long range coupled to F), 7.43–7.73 (m, 7H, benzoyl and C$_4$-H), 6.40 (dd, 1H, 1'-H, J$_{1',2'}$=2.7 Hz, J$_{1',F}$=23.1 Hz), 5.78 (dd, 1H, 3'-H, J$_{3',F}$=19.0Hz, J$_{3',4'}$=3.8 Hz), 5.39 (dd, 1H, 2'-H, J$_{1',2'}$=2.7 Hz, J$_{2',F}$=50.3 Hz), 4.91 (m, 2H, 5'-H), 4.57 (q, 1H, 4'-H, J$_{3',4'}$=3.6 Hz); HRMS m/z calcd. for $C_{26}H_{18}Cl_3FN_2O_5$ 562.0265, found 562.0254. Anal. Calcd. for $C_{26}H_{18}Cl_3FN_2O_5$: C, 55.39, H, 3.22, N, 4.97; found C, 55.38, H, 3.23, N, 4.83.

Compound 6

2,5,6-Trichloro-1-(2-deoxy-2-fluoro-β-D-arabinofuranosyl)benzimidazole (6)

Compound 12 (0.5 g, 0.9 mmol) was dissolved in methanolic ammonia and the solution was stirred at room temperature for 6 hr. The solvent was removed in vacuo and the residue purified by flash chromatography (EtOAc/hexane 5:1, 2 cm×15 cm), appropriate fractions pooled and evaporated to dryness to give after crystallization from MeOH, 0.23 g (74%) of a white solid identical to the previously characterized compound 6.

Figure 3:
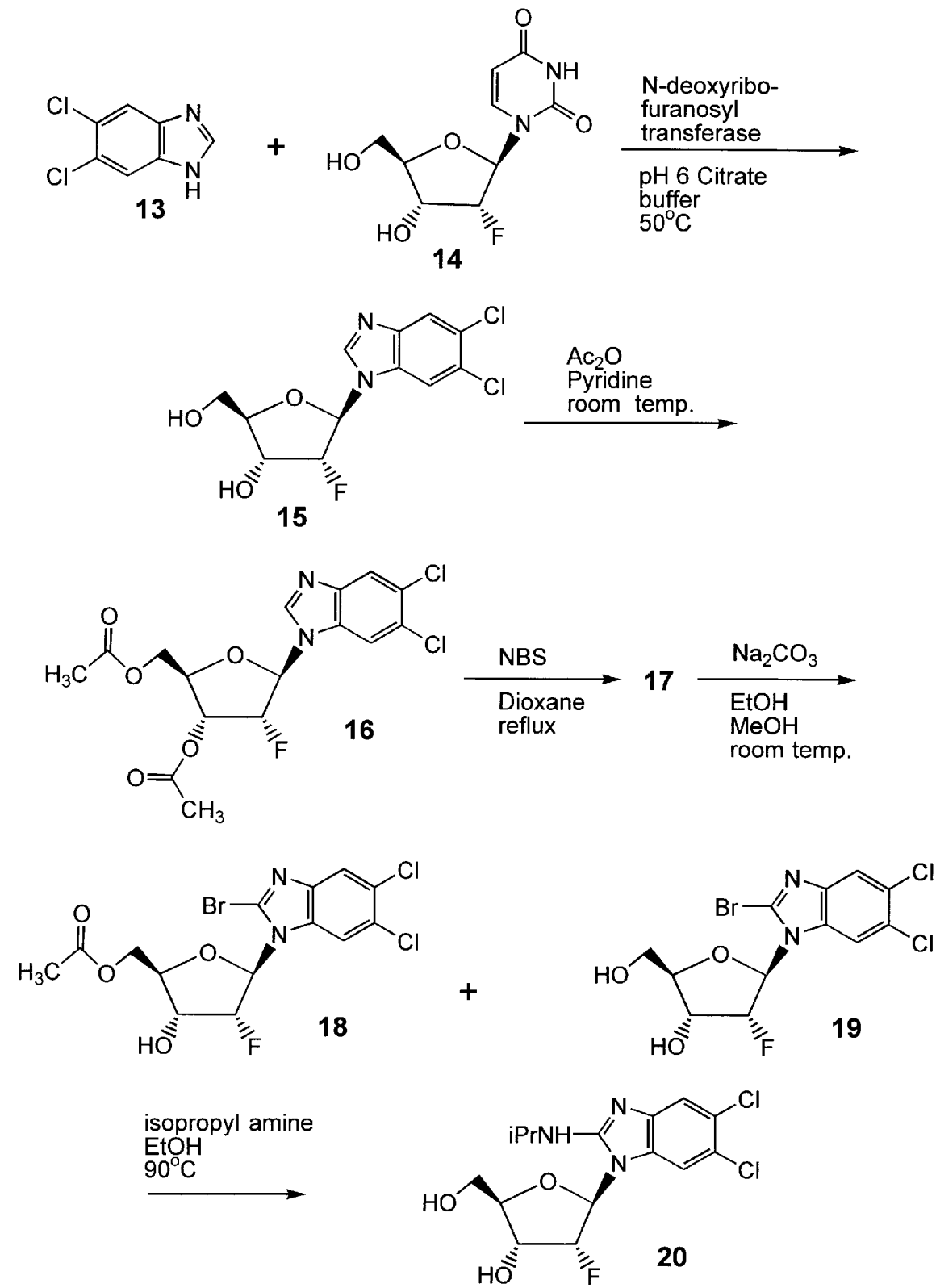
FIG. 3 is a flowchart illustrate still another method for the chemical synthesis of modified benzimidazole nucleosides possessing a fluorinated sugar-like moiety.

Yet another method for the synthesis of a modified benzimidazole nucleoside is illustrated in FIG. 3. In this method, a uridine derivative comprising fluorinated sugar-like moiety is reacted with a benzimidazole in the presence of the enzyme N-deoxyribo-furanosyl transferase to form the desired compound. The benzimidazole moiety of this compound may be further derivatized, for example at the 2-position to yield 2-substituted benzimidazole nucleosides (e.g., 2-Br, 2-NR$_2$).

Compound 15

5,6-Dichloro-1-(2-deoxy-2-fluoro-β-D-ribofuranosyl)benzimidazole (15)

2'-Deoxy-2'-fluorouridine, compound 13 (0.99 g, 4 mmol), which can be prepared by the method of Codington et al. (Codington et al., 1968), was dissolved in 800 mL of 50 mM pH 6.0 citrate buffer. 5,6-dichlorobenzimidazole, compound 14 (0.30g, 1.6 mmoles), which can be prepared by the method of Townsend et al. (Townsend et al., 1970), was added and the reaction was placed in a 50° C. water bath. N-deoxyribo-furanosyl transferase (60,000 units; see Cook et al., 1990) was added and the reaction mixture was gently shaken overnight. 5,6-dichlorobenzimidazole, compound 14 (0.30 g, 1.6 mmoles) was added and the reaction continued for 2 days. The enzyme was precipitated by heating to 80° C. followed by cooling to room temperature. Celite® (50–60 g) was added and the reaction mixture filtered. The product was extracted with ethyl acetate (3×). The ethyl acetate was removed in vacuo and the residue purified by chromatography on 75 g of basic alumina eluted with chloroform/methanol (95:5, v/v) followed by (9:1, v/v), then (2:1, v/v), and finally (1:1, v/v). The product containing fractions were combined and the solvents removed in vacuo to give 0.54 g (67%) of compound 15.

Compound 15: MS (FAB+) m/z, 321, M+1. $^1$H-NMR (DMSO-d$_6$) δ 8.62 (s, 1H, H-2), 8.19 (s, 1H, Ar—H), 7.96 (s, 1H, Ar—H), 6.35 (dd, 1H, H-1', $J_{1',2'}$=3.5 Hz, $J_{1',F}$=14.9 Hz), 5.74 (br s, 1H, OH), 5.23 (dt, 1H, H-2', $J_{1',2'}$=3.5 Hz, $J_{2',3'}$=4.4 Hz, $J_{2',F}$=52.4 Hz), 5.23 (br s, 1H, OH), 4.35 (dt, 1H, H-3', $J_{2',3'}$=4.4 Hz, $J_{3',4'}$=5.3 Hz, $J_{3',F}$=15.9 Hz), 3.98 (m, 1H, H-4'), 3.66 (dd, 2H, H-5', J=3.4 Hz, J=12.5 Hz).

Compound 16

5,6-Dichloro-1-(2-deoxy-2-fluoro-3,5-diacetyl-β-D-ribofuranosyl)benzimidazole (16)

Compound 15 (0.45 g, 1.4 mmol) was dissolved in pyridine (20 mL) and boiled to remove water. The solution was chilled to 0° C. in an ice bath. Acetic anhydride (260 μL, 2.9 mmol, 2 equiv.) was added and the reaction mixture was allowed to warm to room temperature while stirring overnight. Methanol (3 mL) was added and the solvents removed in vacuo. Residual pyridine was removed by coevaporation with toluene (3×). The residue was partitioned between water and the ethyl acetate. The ethyl acetate solution was dried with magnesium sulfate, filtered, and the solvent removed in vacuo to yield 0.56 g (98%) of compound 16. The product was used without further purification.

Compound 16: MS (FAB+) m/z, 405, M+1. $^1$H-NMR (DMSO-d$_6$) δ 8.59 (s, 1H, H-2), 8.05 (s, 1H, Ar—H), 8.01 (s, 1H, Ar—H), 6.45 (dd, 1H, H-1', $J_{1',2'}$=4.8 Hz, $J_{1',F}$=14.8 Hz), 5.75 (dt, 1H H-2', J=5.2 Hz, $J_{2',F}$=51 Hz), 5.40 (m, 1H, H-3'), 4.43 (m,1H, H-4'), 4.28 (m, 2H, H-5'), 2.13 (s, 3H, acetyl-CH$_3$), 2.02 (s, 3H, acetyl-CH$_3$).

Compounds 17, 18, and 19

2-Bromo-5,6-dichloro-1-(2-deoxy-2-fluoro-3,5-diacetyl-β-D-ribofuranosyl)benzimidazole (17), 2-Bromo-5,6-dichloro-1-(2-deoxy-2-fluoro-5-diacetyl-β-D-ribofuranosyl)benzimidazole (18), and 2-Bromo-5,6-dichloro-1-(2-deoxy-2-fluoro-β-D-ribofuranosyl)benzimidazole (19)

Compound 16 (0.55 g, 1.4 mmol) was dissolved in dioxane (25 mL) and boiled to remove water. The solution was heated to reflux in a 120° C. oil bath. N-bromosuccinimide (NBS, 0.48 g, 2.8 mmol, 2 equiv.) was added and the reaction mixture refluxed for 4 min. A second portion of NBS (0.48 g, 2.8 mmol, 2 equiv.) was added and the reflux continued for 6 min. The reaction mixture was removed from the heat, diluted with chloroform (40 mL) and cooled to room temperature. The solution was washed with saturated sodium bicarbonate (2×), dried with magnesium sulfate, and filtered. The solvents were removed in vacuo and the residue purified by chromatography on 75 g of silica gel eluted with ethyl acetate/hexane (1:1, v/v). The product containing fractions were combined and the solvents removed in vacuo to give compound 17. Hydrolysis of the acetyl groups was accomplished by treatment in methanol and ethanol (17 mL each) with sodium carbonate (0.22g, 2.1 mmol, 2 equiv.) dissolved in 4.2 mL water. The reaction mixture was stirred at room temperature overnight. The solution was diluted with water (40 mL). The products were extracted with ethyl acetate (2×). The ethyl acetate solution was dried with magnesium sulfate, filtered, and the solvent removed in vacuo. The residue was purified by chromatography on 75 g of silica gel eluted with ethyl acetate/hexane (1:4, v/v) followed by (1:2, v/v). The faster eluting product was the 5'-acetyl compound, compound 18 (0.17 g) and the second product to elute was the dihydroxy compound, compound 19 (0.03 g).

Compound 18: MS (FAB+) m/z, 399, M+1. $^1$H-NMR (DMSO-d$_6$) δ 8.46 (s, 1H, Ar—H), 7.95 (s, 1H, Ar—H), 6.22 (dd, 1H, H-1', $J_{1',2'}$=5.4 Hz, $J_{1',F}$=14.5 Hz), 5.82 (d, 1H, OH-3', J=5.6 Hz), 5.45 (t, 1H, OH-5', J=4.5 Hz), 5.29 (dt, 1H, H-2', J=5.2 Hz, $H_{2',F}$=53 Hz), 4.3 (m, 1H, H-3'), 4.0 (m, 1H, H-4'), 3.7 (m, 2H, H-5').

Compound 19:$^1$H-NMR (DMSO-d$_6$) δ 8.00 (s, 1H, Ar—H), 7.90 (s, 1H, Ar—H), 6.25 (dd, 1H, H-1', $J_{1',2'}$=5.1 Hz, $J_{1',F}$=16.5 Hz), 5.95 (d, 1H, OH-3', J=6 Hz), 5.40 (dt, 1H, H-2', J=5.3 Hz, $J_{2',F}$=53 Hz), 4.4–4.1 (m, 4H, H-3',4',5'), 2.13 (s, 3H, CH$_3$-acetyl).

Compound 20

2-Isopropylamino-5,6-dichloro-1-(2-deoxy-2-fluoro-β-D-ribofuranosyl)benzimidazole (20)

Compound 18 (0.06 g, 0.14 mmol) was dissolved in ethanol (4 mL) and isopropylamine (1.3 mL) was added. The reaction mixture was heated in a sealed in a 90° C. oil bath for 17 hr. The solvents were removed in vacuo and the residue purified by chromatography on silica gel (6 g) eluted with chloroform/methanol (95:5, v/v). The product containing fractions were combined and the solvents removed in vacuo, giving compound 20 (0.03 g, 57%).

Compound 20: MS (APCH+) m/z, 378, M+1. $^1$H-NMR (DMSO-$d_6$) δ 7.66 (s, 1H, H-2), 7.37 (s, 1H, Ar—H), 6.92 (d, 1H, NH J=7.7 Hz), 6.17 (dd, 1H, H-1', $J_{1',2'}$=5.3 Hz, $J_{1',F}$=15.4 Hz), 5.73 (d, 1H, OH-3', J=5.7 Hz), 5.63 (t, 1H, OH-5', J=4.3 Hz), 5.12 (dt, 1H, H-2', J=5.3 Hz, $J_{2',F}$=53 Hz), 4.29 (dt, 1H, H-3'), 4.02 (m, 1H, CH), 3.94 (m, 1H, H-4'), 3.68 (m, 2H, H-5'), 1.16 (d, 6H, $CH_3$, J=6.5 Hz).

D. Assays for Antiviral Activity and Cytotoxicity

Cells and Viruses

KB cells (available from the American Type Culture Collection (ATCC) 12301 Parklawn Drive, Rockport, Md. 20852 (ATCC CCL 17)), an established human cell line derived from an epidermal oral carcinoma, were grown in minimal essential medium (MEM) (Sigma) with Hanks salts (MEM(H)) supplemented with 5% fetal calf serum. Human foreskin fibroblasts (HFF cells) (provided by the University of Michigan Hospital) and African green monkey kidney cells (BSC-1) (ATTC CCL 26) cells were grown in MEM with Earl salts (MEM(E)) supplemented with 10% fetal bovine serum. Cells were passaged according to conventional procedures and as described in Shipman et al. (Shipman et al., 1976). Briefly, cells were passaged at 1:2 to 1:10 dilutions according to conventional procedures by using 0.05% trypsin plus 0.02% EDTA in a HEPES buffered salt solution. HFF cells were passaged only at 1:2 dilutions.

A plaque purified isolate, $P_o$, of the Towne strain of HCMV was used in all experiments and was a gift of Dr. Mark Stinski, University of Iowa. The KOS strain of HSV-1 was used and was provided by Dr. Sandra K. Weller, University of Connecticut. Stock preparations of HCMV and HSV-1 were prepared and titered as known to those of skill and the art and described in Turk et al. (Turk et al., 1987) and Shipman et al. (Shipman et al., 1990). Briefly, high titer HSV-1 stocks were prepared as follows. Nearly confluent monolayer cultures of KB cells were grown in 32 oz. glass bottles containing MEM(E) buffered with 25 mM HEPES and supplemented with 5% fetal bovine serum and 0.127 g/liter L-arginine (VGM, virus growth medium). The cultures were infected at a low input multiplicity to reduce the formation of defective virus. After cell cytopathology reached "three to four plus", the cells were harvested by vigorous shaking, and concentrated by centrifugation (800×g for 5 min.). The resulting virus pools were stored at −76° C. until retrieved for use in experiments.

HSV-1 was titered using monolayer cultures of BSC-1 cells. Cells were planted at $3 \times 10^5$ cells/well using 6-well cluster dishes. MEM(E) supplemented with 10% fetal bovine serum was employed as medium. After 22–24 hr, cells were 90% confluent and were inoculated in triplicate using at least three ten-fold dilutions with 0.2 ml of the virus suspension to be assayed and incubated in a humidified 4% $CO_2$–90% air atmosphere for one hour to permit viral adsorption. Following virus adsorption, the cell sheet was overlayed with 5 ml of MEM(E) with 5% serum plus 0.5% methocel (4000 CPS) and incubated an additional two to three days. Cells were fixed and stained with 0.1% crystal violet in 20% methanol and macroscopic plaques enumerated.

Stock HCMV was prepared by infecting HFF cells at a multiplicity of infection (m.o.i.) of less that 0.01 plaque-forming units (p.f.u.) per cell. Cell growth medium was changed every four days until cytopathology was evident in all cells (approximately 21 days). Supernatant fluids were retained as the virus stock. Four days later, the remaining cells were disrupted by three cycles of freeze-thawing and the cell plus medium held as an additional source of virus. Storage was in liquid nitrogen.

HCMV was titered in 24-well cluster dishes which were plated to contain $5 \times 10^4$ HFF cells/well, grown as described above. When the cells were 70 to 80% confluent, 0.2 ml of the virus suspension was added per well and adsorbed as described above. At least three ten-fold dilutions of each preparation were used. Following virus adsorption, the cell sheets were overlayed with 0.5% methocel (4000 CPS) in maintenance medium [MEM(E) with 1.1 g/liter $NaHCO_3$, 100 units/ml penicillin G, 100 μg/ml streptomycin, and 5% fetal bovine serum]. The cultures were incubated in a humidified atmosphere of 4% $CO_2$–96% air. Viral plaques were visible 5 to 7 days after infection using at least 10-fold magnification. Cells were fixed and stained by a 10-minute exposure to a 0.1% solution of crystal violet in 20% methanol 7 to 12 days after infection. Microscopic foci were enumerated at 20-fold magnification using a Nikon Profile Projector.

Assays for Antiviral Activity

HCMV plaque and yield reduction experiments were performed with monolayer cultures of HFF cells by a procedure similar to that referenced above for titration of the viruses and described in Townsend et al. (Townsend et al., 1995). Activity of compounds against HSV-1 was evaluated using an ELISA assay, also described in Townsend et al. (Townsend et al., 1995).

The effect of compounds of the replication of HCMV was measured using plaque and yield reduction assays. For the former, HFF cells in 24-well culture dishes were infected with approximately 50 p.f.u. of HCMV per well using the procedures detailed above. Compounds dissolved in growth medium were added in four to six selected concentrations to duplicate wells following virus adsorption. Following incubation at 37° C. for 7 to 10 days, cell sheets were fixed, stained and microscopic plaques were enumerated as described above. Drug effects were calculated as a percentage of reduction in number of plaques in the presence of each drug concentration compared to the number observed in the absence of drug. DHPG (ganciclovir) was used as a positive control in all experiments. Yield reduction assays were performed as described in Townsend et al. (Townsend et al., 1995).

ELISA techniques, as described in Townsend et al. (Townsend et al., 1995) were used to determine activity against HSV-1. Drug effects were calculated as a percentage of the reduction in virus titers in the presence of each drug concentration compared to the titer obtained in the absence of drug. Acyclovir was used as a positive control in all experiments.

Assays for Cytotoxicity

Two different methods were used to evaluate cytotoxicity of the compounds. First, cytotoxicity produced in stationary HFF cells was determined by microscopic examination of cells not affected by the virus used in the plaque assay. Second the effect of compounds on KB cells during two population doubling times was determined by crystal violet staining and spectrophotometric quantitation of dye eluted from stained cells. This method has been utilized for the analysis of ganciclovir and zidovudine (See Prichard et al., 1991).

Antiviral activity and cytotoxicity data for two of the fluorinated sugar benzimidazole nucleosides of the present invention are presented in Table 1, along with comparison data for known antiviral agents TCRB and ganciclovir.

TABLE 1

50% Inhibitory Concentration $IC_{50}$ (μM)

| Compound | Antiviral Activity HCMV | | HSV-1 | Cytotoxicity | |
|---|---|---|---|---|---|
| | Plaque | Yield | (ELISA assay) | Visual (HFF cells) | Growth (KB cells) |
| Compound 2 | >10 | — | >100 | >10 | >10 |
| Compound 3 | >10 | — | >100 | >10 | >10 |
| Compound 6 2'-F-ara-TCRB | 13.0 | 8 | 50 | 32 | 60 |
| Compound 7 3'-F-xylo-TCRB | 9.4 | 13 | >100 | 40 | >100 |
| Compound 12 | 23 | — | >100 | >10 | >100 |
| Ganciclovir (DHPG) | 7.4 ± 6.5 | 1.6 ± 1.2 | 3.5 ± 2.1 | >100 | >100 |
| TCRB (Compound 1) | 2.76 | 1.3 ± 0.8 | 151 | 238 | 175 |
| BDCRB | 0.48 | — | — | 141 | — |

Antiviral activity and cytotoxicity data for three of the fluorinated sugar benzimidazole nucleosides of the present invention are presented below in Table 2.

HCMV strain AD169 was grown on monolayers of human embryonic lung cells (MRC5 cells) in 96 well plates. After injection of the cells at a ratio of approximately 0.01 infectious virus particles per cell, the compounds to be tested were added to selected wells at six different concentrations, each in triplicate. The same concentrations of compounds were also applied to wells containing monolayers of uninfected cells in order to assess compound cytotoxicity. The plates were incubated for 5 days, and the minimum cytotoxic dose was estimated from microscopic examination. The $IC_{50}$ for antiviral effect was estimated from measurements of HCMV DNA in each well by blotting and quantitative specific DNA hybridization, similar to the method of Gadler (see, Gadler, 1983).

Briefly, the probe for hybridization was prepared from cosmids pC7531 and pCS37 (see, Sullivan et al., 1993). These contain the HCMV AD169 sequences from nucleotides 102,000 to 143,300 and 51,600 to 92,900, respectively. The probe is a 1:1 mixture of the two cosmids labeled with α-[$^{32}$P]-dCTP using random primers and T7 DNA polymerase (Pharmacia) after cutting with nuclease Xbal. The probe was denatured by heating for 2 minutes at 99° C. and filtered through a sterile Corning 0.45 μm filter (25933–200).

Prehybridization of the membranes was carried out in 6x SSPE (SSPE: 0.18M NaCl, 10 mM $NaPO_4$ (pH 7.7), 1 mM EDTA), 1% Ficoll, 1% polyvinylpyrrolidine, 1% BSA, 0.5% SDS, and 50 μg/mL salmon sperm DNA at 45° C. for 2 to 12 hr.

The prehybridization solution was replaced with hybridization solution (6x SSPE, 0.5% SDS, 50 μg/mL salmon sperm DNA) containing 1×10$^6$ cpm/mL of each heat-denatured probe. Hybridization was for 16 hr at 65° C. The membranes were then washed as follows: 6x SSPE with 0.5% SDS, room temperature, 2x for 2 min; 1x SSPE with 0.5% SDS, 65° C., 2x for 15 min; 0.1x SSPE with 0.5% SDS, 65° C., once for 1 hr.

The membranes were blotted dry and wrapped in Saran wrap for quantitation by PhosphoImager (Molecular Dynamics, Sunnyvale, Calif.). The PhosphoImager screens were exposed to the blots for 16 to 24 hr. The gross counts in each sample were calculated using ImageQuant software (Molecular Dynamics, Sunnyvale, Calif.) and net counts obtained by subtracting the local membrane background.

The counts of the drug dilution wells were compared to the counts of untreated control wells to produce a response curve and were used to calculate the $IC_{50}$ values. The $IC_{50}$ values were calculated by weighted linear regression according to the Hill equation.

TABLE 2

50% Inhibitory Concentration $IC_{50}$ (μM)

| Compound | Antiviral Activity HCMV (DNA Hybridization) | Cytotoxicity (MRC5 cells) |
|---|---|---|
| Compound 15 | 12.5 ± 0.7 | >100 |
| Compound 19 | 13.7 ± 0.5 | 72.8 |
| Compound 20 | 8.9 ± 2.7 | 49.0 |

The embodiments of this invention illustrated above are intended to aid in an understanding of the invention but are not intended to, and should not be construed to, limit in any way the invention as set forth in the following claims. Other aspects, advantages and modifications within the scope of this invention will be apparent to those skilled in the art to which this invention pertains.

E. References

The disclosures of the publications, patents, and published patent specifications referenced below are hereby incorporated by reference into the present disclosure to more fully describe the state of the art to which this invention pertains.

Blank, H. U.; Frahne, D.; Myles, A.; Pfleiderer, W. Uber die Tritylierung von Adenosin-Derivate. *Liebigs Ann. Chem.* 1970, 742, 34–42.)

Chu, C. K.; Matulic-Adamic, J.; Huang, J.-T.; Chou, T-C.; Burchenal, J. H.; Fox, J. J.; Watanabe, K. A., "Nucleosides 135. Synthesis of Some 9-(2-deoxy-2-fluoro-β-D-arabinofurnosyl)-9H-purines and Their Biological Activities," *Chem. Pharm. Bull.* 1989, 37, 336.

Codington, J. F., Doerr, I. L., Fox, J. J., *J. Org. Chem.*, 1964, vol. 29, pp. 558.

Cook et al., *J. Biol. Chem.*, (1990), Vol. 265, p. 2682.

Devivar, R. V. et al. (1994) *J. Med. Chem.* Vol. 37:2942–2949.

Gadler, Antimicrob. Agents Chemother., 1983, vol. 24, pp. 370–374.

Good et al., *Antiviral Research* (Suppl. 1), Vol. 23, p. 103 (1994).

Herdewijn, P.; Aerchot, A.; Kerremans, L. Synthesis of Nucleosides Fluorinated in the Sugar Moiety. The Application of Diethylaminosulfur Trifluoride to the Synthesis of Fluorinated Nucleosides. *Nucleosides and Nucleotides* 1989, 8, 65–96 and references therein.

Howell et al., *J. Org. Chem.*, 1995, Vol. 50, p. 3644–3647.

Howell, H. G.; Brodfuehrer, P. R.; Brundige, S. P.; Benigne, D. A.; Sapino, C. Antiviral Nucleosides. A Stereospecific, Total Synthesis of 2'-Fluoro-2'-deoxy-β-D-arabinofuranosyl Nucleosides. *J. Org. Chem.* 1988, 53, 85–88.

Krezeminski, J.; Nawrot, B.; Pankiewicz, K. W.; Watanabe, K. A. Synthesis of 9-(2-Deoxy-2-fluoro-β-D-arabinofuranosyl)hypoxanthine. The First Direct Introduction of a 2'-β-Fluoro Substituent in Preformed Purine Nucleosides. Studies Directed Toward The Synthesis of 2'-Deoxy-2'-Substituted Arabinonucleosides. *Nucleosides and Nucleotides* 1991, 19, 781–798.

Montgomery, J. A.; Shortnacy, A. T.; Carson, D. A.; Secrist III, J. A. 9-(2-Deoxy-2-fluoro-β-D-arabinofuranosyl) guanine: A Metabolically Stable Cytotoxic Analogue of 2'-Deoxyguanosine. *J. Med. Chem.* 1986, 29, 2389–2392.

Pankiewicz, K. W.; Krzeminski, J.; Ciszewski, L. A.; Ren, W. Y.; Watanabe, K. A., "A Synthesis of 9-(2-Deoxy-2-fluoro-β-D-arabinofuranosyl)adenine and Hypoxanthine. An Effect of C3'-Endo to C2'-Endo Conformational Shift on the Reaction Course of 2'-Hydroxyl Group with DAST," *J. Org. Chem.* 1992, 57, 553–559.

Pankiewicz, K. W.; Watanabe, K. A. A Synthesis of 2'-Fluoro- and 3'-Fluoro-Substituted Purine Nucleosides via a Direct Approach. In Nucleosides as Antitumor and Antiviral Agents; Chu, C. K.; Baker, D. C., Eds.; Plenum Press: New York, 1993, pp 55–71.

Prichard, M. N. et al. *Antiviral Res.* (1991) Vol. 35:1060–1065.

Reichman, U.; Watanabe, K. A.; Fox, J. J. A Practical Synthesis of 2-Deoxy-2-Fluoro-D-Arabinofuranose Derivatives. *Carbohydr. Res.* 1975, 42, 233–240

Revenkar, R. G. and Townsend, L. B. (1968) *J. Heterocyclic Chem.* Vol. 5:477–483

Revenkar, R. G. and Townsend, L. B. (1968) *J. Heterocyclic Chem.* Vol. 5:615–620;

Saluja, S. et al. "Synthesis and antiviral activity of certain 2-substituted-5,6-dichlorobenzimidazole acyclic nucleosides. Poster #146. Division of Medicinal Chemistry, 204th American Chemical Society National Meeting, Washington, D.C., Aug. 23–28, 1992.

Shipman, C., Jr. et al. (1976) Antimicrob. Agents Chemother. Vol. 9:120

Shipman, C., Jr., et al. (1990) J. Virol. Methods Vol. 28:101–106.

Still, W. C.; Kahn, M.; Mitra, A., "Rapid Chromatographic Techniques for Preparative Separation with Moderate Resolution," *J. Org. Chem.* 1978, 43, 2923–2925.

Tamm, I., *Science* (1954) Vol. 120:847–848).

Tann, C. H.; Brodfuehrer, P. R.; Brundige, S. P.; Sapino, C.; Howell, H. G. Fluorocarbohydrates in Synthesis. An efficient Synthesis of 1-(2-Deoxy-2-fluoro-β-D-arabinofuranosyl)-5-iodouracil (β-FIAU) and 1-(2-Deoxy-2-fluoro-β-D-arabinofuranosyl)thymine (β-FMAU). *J. Org. Chem.* 1985, 50, 3644–3647.

Thiem, J.; Rash, D. Synthesis and Perkow Reaction of Uridine Derivatives. *Nucleosides and Nucleotides* 1985, 4, 487.

Townsend and Revankar, *Chem. Rev.*, (1970), Vol.70, p. 389.

Townsend, L. B. and Drach, J. C., Fifth International Conference on Antiviral Research Vancouver, British Columbia, March 1992;

Townsend, L. B., et al., *J. Med. Chem.*, Vol. 38, pp. 4098–4105 (1995).

Townsend, L. B., et al., U.S. Pat. No. 5,248,672 issued 28 Sep. 1993.

Townsend, L. B., et al., U.S. Pat. No. 5,360,795 issued 01 Nov. 1994.

Turk, S. R. et al. (1987) *Antimicrob. Agents Chemother.* Vol. 31:544–550.

V. Sullivan, K. K. Biron, C. L. Talarico, S. C. Stanat, M. G. Davis, L. S. Pozzi, and D. M. Coen, Antimicrob. Agents Chemother., 1993, vol. 37, pp. 19–25.

Wright, J. A.; Taylor, N. F.; Fox, J. J. Nucleosides. LX. Fluorocarbohydrates. XXII.

Synthesis of 2-deoxy-2-fluoro-D-arabinose and 9-(2-deoxy-2-fluoro-α- and β-arabinofuranosyl)adenines. *J. Org Chem.* 1969, 34, 2632–2636.

Zou, R. et al., "Design, synthesis and antiviral evaluation of some TCRB analogs modified on the benzene moiety," Poster #142. Division of Medicinal Chemistry, 204th American Chemical Society National Meeting, Washington, D.C., Aug. 23–28, 1992.

We claim:

1. A modified benzimidazole nucleoside of the formula:

wherein $R^1$ is selected from the group consisting of:
2'-fluoro-threo-furanosyl; 3'-fluoro-threo-furanosyl;
2'-fluoro-erythro-furanosyl; 3'-fluoro-erythro-furanosyl;
2'-fluoro-ribo-furanosyl; 3'-fluoro-ribo-furanosyl;
2'-fluoro-ara-furanosyl; 3'-fluoro-ara-furanosyl;
2'-fluoro-xylo-furanosyl; and 3'-fluoro-xylo-furanosyl;

$R^2$ is —H, —F, —Cl, —Br, —I, or —NR$_2$,
wherein R is independently —H or an alkyl group having 1–6 carbon atoms;

$R^4$ is —H, —F, —Cl, —Br, or —I;
$R^5$ is —H, —F, —Cl, —Br, or —I;
$R^6$ is —H, —F, —Cl, —Br, or —I;
$R^7$ is —H, —F, —Cl, —Br, or —I;
or a pharmaceutically acceptable salt thereof.

2. The modified benzimidazole nucleoside of claim 1, wherein $R^1$ is selected from the group consisting of:
2'-fluoro-ribo-furanosyl;
2'-fluoro-ara-furanosyl; and
3'-fluoro-xylo-furanosyl.

3. The modified benzimidazole nucleoside of claim 2, wherein $R^2$ possesses one or more hydroxyl groups in a protected form as an acetate, benzoate, or trityl ether.

4. The modified benzimidazole nucleoside of claim 1, wherein $R^1$ is 2'-fluoro-ara-furanosyl; $R^2$ is —Cl; $R^4$ is —H; $R^5$ is —Cl; $R^6$ is —Cl; and $R^7$ is —H.

5. The modified benzimidazole nucleoside of claim 1, wherein $R^1$ is 3'-fluoro-xylo-furanosyl; $R^2$ is —Cl $R^4$ is —H; $R^5$ is —Cl; $R^6$ is —Cl; and $R^7$ is —H.

6. The modified benzimidazole nucleoside of claim 1, wherein $R^1$ is 2'-fluoro-ribo-furanosyl; $R^2$ is —H; $R^4$ is —H; $R^5$ is —Cl; $R^6$ is —Cl; and $R^7$ is —H.

7. The modified benzimidazole nucleoside of claim 1, wherein $R^1$ is 2'-fluoro-ribo-furanosyl; $R^2$ is —Br; $R^4$ is —H; $R^5$ is —Cl; $R^6$ is —Cl; and $R^7$ is —H.

8. The modified benzimidazole nucleoside of claim 1, wherein $R^1$ is 2'-fluoro-ribo-furanosyl; $R^2$ is —NH(CH(CH$_3$)$_2$); $R^4$ is —H; $R^5$ is —Cl; $R^6$ is —Cl; and $R^7$ is —H.

9. An antiviral composition comprising an effective amount of a compound according to claim 1 and a pharmaceutically acceptable carrier.

10. A method of inhibiting herpes virus proliferation in a herpes virus infected cell comprising contacting the cell with an effective amount of a compound according to claim 1 under suitable conditions such that herpes virus proliferation is inhibited.

11. A method of inhibiting HCMV proliferation in a HCMV infected cell comprising contacting the cell with an effective amount of a compound according to claim 1 under suitable conditions such that HCMV proliferation is inhibited.

12. A method of prophylactically treating a cell susceptible to herpes virus infection, by contacting the cell with an effective amount of a compound according to claim 1 under suitable conditions such that herpes virus infection is prevented.

13. A method of prophylactically treating a cell susceptible to HCMV infection, by contacting the cell with an effective amount of a compound according to claim 1 under suitable conditions such that HCMV infection is prevented.

* * * * *

(12) REEXAMINATION CERTIFICATE (4710th)
United States Patent
Townsend et al.

(10) Number: US 5,840,743 C1
(45) Certificate Issued: Jan. 7, 2003

(54) MODIFIED BENZIMIDAZOLE NUCLEOSIDES AS ANTIVIRAL AGENTS

(75) Inventors: Leroy B. Townsend, Ann Arbor, MI (US); John C. Drach, Ann Arbor, MI (US); George A. Freeman, Raleigh, NC (US)

(73) Assignees: Glaxo Wellcome Inc., Research Triangle Park, NC (US); The Regents of the University of Michigan, Ann Arbor, MI (US)

Reexamination Request:
No. 90/006,246, Mar. 13, 2002

Reexamination Certificate for:
Patent No.: 5,840,743
Issued: Nov. 24, 1998
Appl. No.: 08/786,696
Filed: Jan. 22, 1997

Related U.S. Application Data
(60) Provisional application No. 60/010,463, filed on Jan. 23, 1996.

(51) Int. Cl.$^7$ .................. A61K 31/4184; C07D 405/04
(52) U.S. Cl. .................. 514/394; 514/394; 548/304.7

(56) References Cited

PUBLICATIONS

Atrazhev et al., Bioorganic Chemistry, vol. 13, No. 10 (1997) pp. 1374–1381, original Russian text and full certified English translation.

*Primary Examiner*—Evelyn Huang

(57) ABSTRACT

This invention pertains to nucleoside analogs which have antiviral activity and improved metabolic stability. More specifically, this invention pertains to modified sugar benzimidazole nucleosides, as exemplified by compounds such as benzimidazole nucleosides possessing a fluorinated sugar-like moiety (for example, a 2'-fluoro-furanosyl moiety or a 3'-fluoro-furanosyl moiety), and may be represented by the following formula,

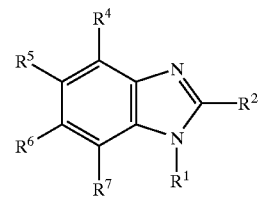

wherein $R^1$ is a fluorinated sugar-like moiety; and $R^2$, $R^4$, $R^5$, $R^6$ and $R^7$ are benzimidazole substituents, such as —H, halogens (e.g., —F, —Cl, —Br, —I), —$NO_2$, —$NR_2$ (where R is independently —H or an alkyl group having 1–6 carbon atoms), —OR (where R is —H or an alkyl group having 1–6 carbon atoms), —SR (where R is —H or a hydrocarbyl of 1–10 carbon atoms), and —$CF_3$. In one emdobiment, $R^1$ is 2'-fluoro-furanosyl or 3'-fluoro-furanosyl; $R^2$ is —H, —F, —Cl, —Br, —I, or —$NR_2$, wherein R is independently —H or an alkyl group having 1–6 carbon atoms; $R^4$, $R^5$, $R^6$ and $R^7$ are independently —H, —F, —Cl, —Br, or —I.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–13 dependent on an amended claim, are determined to be patentable.

New claims 14–18 are added and determined to be patentable.

1. A modified benzimidazole nucleoside of the formula:

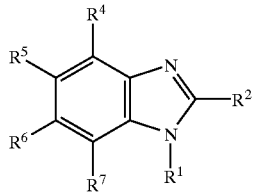

wherein
R$^1$ is selected from the group consisting of:
2'-fluoro-threo-furanosyl; 3'-fluoro-threo-furanosyl; 2'-fluoro-erythro-furanosyl; 3'-fluoro-erythro-furanosyl; 2'-fluoro-ribo-furanosyl; [3'-fluoro-ribo-furanosyl;] 2'-fluoro-ara-furanosyl; 3'-fluoro-ara-furanosyl; 2'-fluoro-xylo-furanosyl; and 3'-fluoro-xylo-furanosyl;
R$^2$ is —H, —F, —Cl, —Br, —I, or NR$_2$, wherein R is independently —H or an alkyl group having 1–6 carbon atoms;
R$^4$ is —H, —F, —Cl, —Br, or —I;
R$^5$ is —H, —F, —Cl, —Br, or —I:
R$^6$ is —H, —F, —Cl, —Br, or —I;
R$^7$ is —H, —F, —Cl. —Br, or —I;
or a pharmaceutically acceptable salt thereof.

14. *An antiviral composition comprising an effective amount of a modified benzimidazole nucleoside of the formula:*

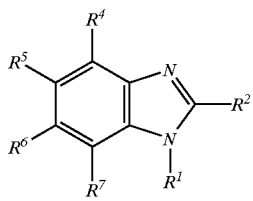

*wherein*
*R$^1$ is selected from the group consisting of:*
*2'-fluoro-threo-furanosyl; 3'-fluoro-threo-furanosyl; 2'-fluoro-erythro-furanosyl; 3'-fluoro-erythro-furanosyl; 2'-fluoro-ribo-furanosyl; 3'-fluoro-ribo-furanosyl; 2'-fluoro-ara-furanosyl; 3'-fluoro-ara-furanosyl; 2'-fluoro-xylo-furanosyl; and 3'-fluoro-xylo-furanosyl;*
*R$^2$ is —H, —F, —Cl, —Br, —I, or NR$_2$, wherein R is independently —H or an alkyl group having 1–6 carbon atoms;*
*R$^4$ is —H, —F, —Cl, —Br, or —I;*
*R$^5$ is —H, —F, —Cl, —Br, or —I;*
*R$^6$ is —H, —F, —Cl, —Br, or —I.*
*R$^7$ is —H, —F, —Cl, —Br, or —I;*
*or a pharmaceutically acceptable salt thereof; and*
*a pharmaceutically acceptable carrier.*

15. *A method of inhibiting herpes virus proliferation in a herpes virus infected cell which comprises contacting the cell with an effective amount of a modified benzimidazole nucleoside of the formula:*

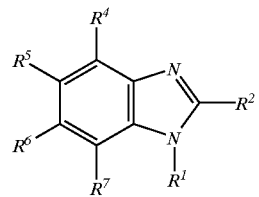

*wherein*
*R$^1$ is selected from the group consisting of:*
*2'-fluoro-threo-furanosyl; 3'-fluoro-threo-furanosyl; 2'-fluoro-erythro-furanosyl; 3'-fluoro-erythro-furanosyl; 2'-fluoro-ribo-furanosyl; 3'-fluoro-ribo-furanosyl; 2'-fluoro-ara-furanosyl; 3'-fluoro-ara-furanosyl; 2'-fluoro-xylo-furanosyl; and 3'-fluoro-xylo-furanosyl;*
*R$^2$ is —H, —F, —Cl, —Br, —I, or NR$_2$, wherein R is independently —H or an alkyl group having 1–6 carbon atoms;*
*R$^4$ is —H, —F, —Cl, —Br, or —I;*
*R$^5$ is —H, —F, —Cl, —Br, or —I:*
*R$^6$ is —H, —F, —Cl, —Br, or —I;*
*R$^7$ is —H, —F, —Cl, —Br, or —I;*
*or a pharmaceutically acceptable salt thereof, under suitable conditions such that the herpes virus proliferation is inhibited.*

16. *A method of inhibiting HCMV proliferation in a HCMV infected cell which comprises contacting the cell with an effective amount of a modified benzimidazole nucleoside of the formula:*

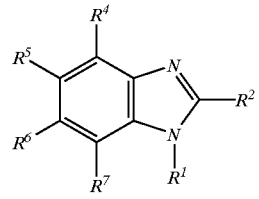

*wherein*
*R$^1$ is selected from the group consisting of:*
*2'-fluoro-threo-furanosyl; 3'-fluoro-threo-furanosyl; 2'-fluoro-erythro-furanocyl; 3'-fluoro-erythro-furanosyl; 2'-fluoro-ribo-furanosyl; 3'-fluoro-ribo-furanosyl; 2'-fluoro-ara-furanosyl; 3'-fluoro-ara-* furanosyl; 2'-fluoro-xylo-furanosyl; and 3'-fluoro-xylo-furanosyl;

$R^2$ is —H, —F, —Cl. —Br, —I, or $NR_2$, wherein R is independently —H or an alkyl group having 1–6 carbon atoms;

$R^4$ is —H, —F, —Cl, —Br, or —I;
$R^5$ is —H, —F, —Cl, —Br, or —I;
$R^6$ is —H, —F, —Cl, —Br, or —I;
$R^7$ is —H, —F, —Cl, —Br, or —I;

or a pharmaceutically acceptable salt thereof, under suitable conditions such that the HCMV proliferation is inhibited.

17. A method of prophylactically treating a cell susceptible to herpes virus infection by contracting the cell with an effective amount of a modified benzimidazole nucleoside of the formula:

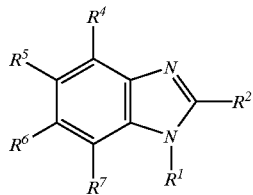

wherein $R^1$ is selected from the group consisting of:
2'-fluoro-threo-furanosyl; 3'-fluoro-threo-furanosyl; 2'-fluoro-erythro-furanosyl; 3'-fluoro-erythro-furanosyl; 2'-fluoro-ribo-furanosyl; 3'-fluoro-ribo-furanosyl; 2'-fluoro-ara-furanosyl; 3'-fluoro-ara-furanosyl; 2'-fluoro-xylo-furanosyl; and 3'-fluoro-xylo-furanosyl;

$R^2$ is —H, —F, —Cl, —Br, —I, or $NR_2$, wherein R is independently —H or an alkyl group having 1–6 carbon atoms;

$R^4$ is —H, —F, —Cl. —Br, or —I;
$R^5$ is —H, —F, —Cl, —Br, or —I;
$R^6$ is —H, —F, —Cl, —Br, or —I;
$R^7$ is —H, —F, —Cl, —Br, or —I;

or a pharmaceutically acceptable salt thereof, under suitable conditions such that herpes virus infection is prevented.

18. A method of prophylactically treating a cell susceptible to HCMV infection by contacting the cell with an effective amount of a modified benzimidazole nucleoside of the formula:

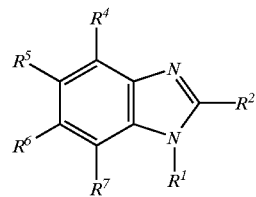

wherein $R^1$ is selected from the group consiting of:
2'-fluoro-threo-furanosyl; 3'-fluoro-threo-furanosyl; 2'-fluoro-erythro-furanosyl; 3'-fluoro-erythro-furanosyl; 2'-fluoro-ribo-furanosyl; 3'-fluoro-ribo-furanosyl; 2'-fluoro-ara-furanosyl; 3'-fluoro-ara-furanosyl; 2'-fluoro-xylo-furanosyl; and 3'-fluoro-xylo-furanosyl;

$R^2$ is —H, —F, —Cl, —Br, —I, or $NR_2$, wherein R is independently —H or an alkyl group having 1–6 carbon atoms;

$R^4$ is —H, —F, —Cl, —Br, or —I;
$R^5$ is —H, —F, —Cl, —Br, or —I;
$R^6$ is —H, —F, —Cl, —Br, or —I;
$R^7$ is —H, —F, —Cl, —Br, or —I;

or a pharmaceutically acceptable salt thereof, under suitable conditions such that HCMV infection is prevented.

* * * * *